(12) United States Patent
Curatu et al.

(10) Patent No.: US 11,314,051 B2
(45) Date of Patent: Apr. 26, 2022

(54) SYSTEM AND METHOD FOR LASER GENERATED CORNEAL AND CRYSTALLINE LENS INCISIONS USING A VARIABLE F/# OPTICAL SYSTEM WITH ASPHERIC CONTACT INTERFACE TO THE CORNEA OR ROTATING AND ADAPTIVE OPTICS

(71) Applicant: Lensar, Inc., Orlando, FL (US)

(72) Inventors: George C. Curatu, Orlando, FL (US); Rudolph W. Frey, Winter Park, FL (US); John McWhirter, Winter Park, FL (US); Steven E. Bott, Oviedo, FL (US)

(73) Assignee: Lensar, Inc., Orlando, FL (US)

( * ) Notice: Subject to any disclaimer, the term of this patent is extended or adjusted under 35 U.S.C. 154(b) by 115 days.

(21) Appl. No.: 16/901,126

(22) Filed: Jun. 15, 2020

(65) Prior Publication Data

US 2020/0379216 A1    Dec. 3, 2020

Related U.S. Application Data

(62) Division of application No. 13/435,103, filed on Mar. 30, 2012, now Pat. No. 10,684,449.

(60) Provisional application No. 61/550,101, filed on Oct. 21, 2011, provisional application No. 61/470,734, filed on Apr. 1, 2011.

(51) Int. Cl.
*G02B 13/00* (2006.01)
*G02B 27/00* (2006.01)
*A61F 9/008* (2006.01)
*G02B 26/10* (2006.01)
*A61F 9/009* (2006.01)

(52) U.S. Cl.
CPC .......... *G02B 13/0005* (2013.01); *A61F 9/009* (2013.01); *A61F 9/00825* (2013.01); *G02B 26/101* (2013.01); *G02B 27/0031* (2013.01); *A61F 2009/0087* (2013.01); *A61F 2009/00872* (2013.01); *A61F 2009/00897* (2013.01)

(58) Field of Classification Search
CPC .............. G02B 13/0005; G02B 15/177; G02B 26/101; G02B 27/0031; A61F 9/008–2009/00897; A61F 9/00–9/013
See application file for complete search history.

*Primary Examiner* — Jonathan T Kuo
(74) *Attorney, Agent, or Firm* — Glen P. Belvis; Belvis Law, LLC.

(57) ABSTRACT

A laser system including a laser source that generates a laser beam and an optical switch that receives the laser beam and selectively sends the laser beam to either a fast path or a slow path, wherein in the fast path the laser beam has a first F/# and in the slow path the laser beam has a second F/# that is higher in value that of the first F/#. The laser system further including an afocal optical system that is in the slow path and receives the laser beam from the optical switch and an x-y scanner that receives either a first laser beam from the slow path or a second laser beam from the fast path. The laser system including a scan lens system that receives a scanning laser beam from the x-y scanner and performs a z-scan for the scanning laser beam only in the case wherein the scanning laser beam is generated from the laser beam in the fast path. The laser system further including an aspheric patient interface device that receives a laser beam from the scan lens system.

17 Claims, 19 Drawing Sheets

Typical incisions/cuts made with fast laser beam (top view).
Note that all these incisions/cuts are circular.

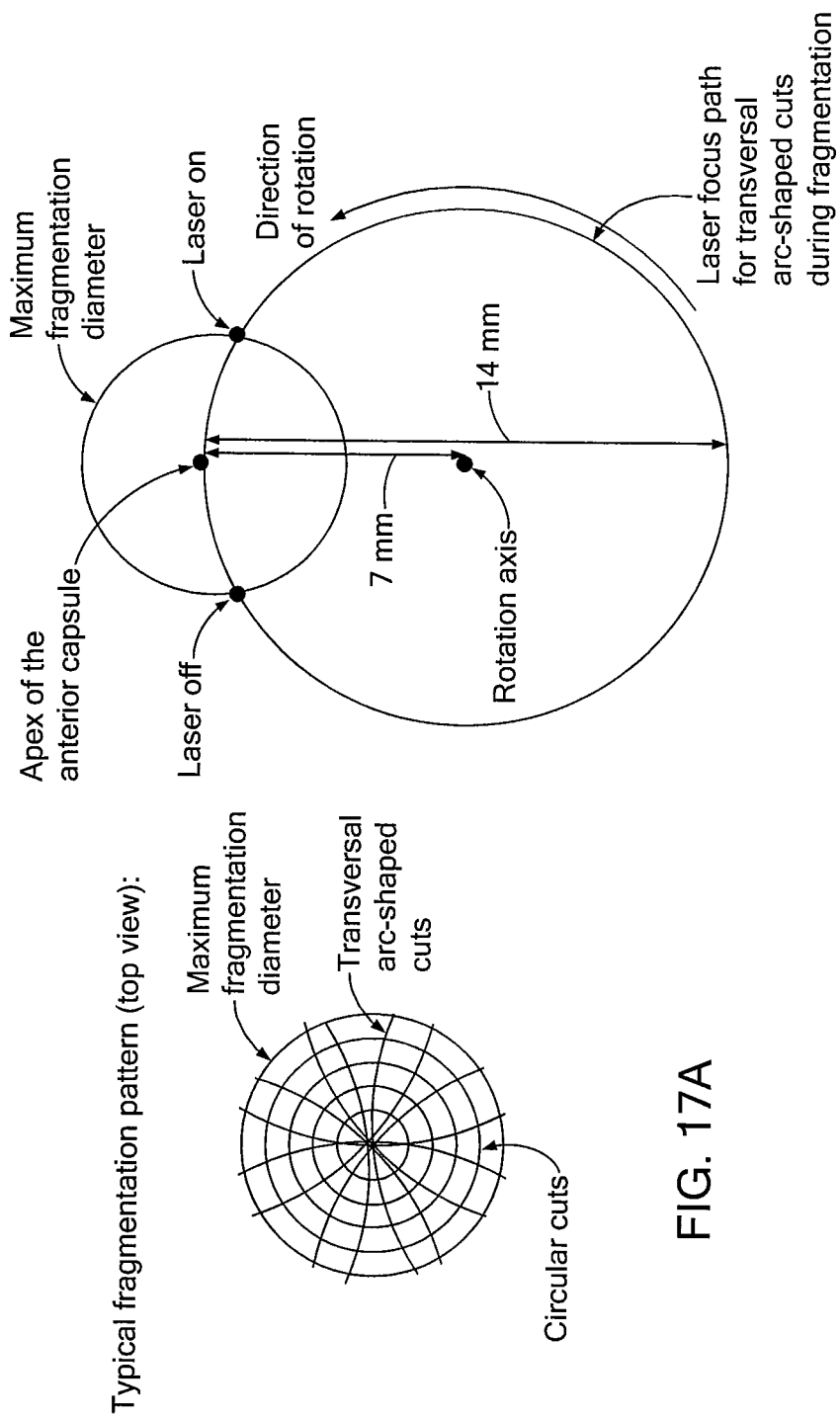

SYSTEM AND METHOD FOR LASER GENERATED CORNEAL AND CRYSTALLINE LENS INCISIONS USING A VARIABLE F/# OPTICAL SYSTEM WITH ASPHERIC CONTACT INTERFACE TO THE CORNEA OR ROTATING AND ADAPTIVE OPTICS

This application is a divisional of U.S. application Ser. No. 13/435,103 filed Mar. 20, 2012, which application claims the benefit of priority under 35 U.S.C. § 119(e)(1) of 1) U.S. Provisional Application Ser. No. 61/470,734, filed Apr. 1, 2011 and 2) U.S. Provisional Application Ser. No. 61/550,101, filed Oct. 21, 2011, the entire contents of each of which is incorporated herein by reference.

FIELD OF THE INVENTION

The present invention relates to a system and method for laser generated corneal and crystalline lens incisions.

BACKGROUND

Recently, femtosecond laser systems are emerging as an alternative to manual incisions in the cornea and crystalline lens for different ophthalmic surgeries. Examples of such laser systems are the Intralase FS Laser and IFS Advanced Femtosecond Laser manufactured and sold by Abbott Medical Optics of Abbott Park, Ill. and the LenSx Femtosecond Laser manufactured and sold by LenSx Lasers of Aliso Viejo, Calif. Such lasers make incisions by focusing ultrashort laser pulses to a very fine focus, causing a plasma mediated photodisruption of the tissue at the points of focus. The incision is generated by placing a contiguous series of such pulses in the pattern of the desired incision. The combined effect of the pattern of pulses is cleaving the tissue at the targeted plane. Arbitrarily complex incision patterns can be generated with such lasers. Furthermore, femtosecond lasers are believed to make more accurate and consistent incisions than the incisions formed manually.

The image space F/# of a beam delivery optical system, such as the femtosecond laser systems described previously, is defined as the focal length relative to the aperture of the system (F/#=f/D, wherein f is the focal length of the beam delivery optical system and D is the entrance pupil diameter). The diameter of a laser spot formed by a beam delivery system is directly proportional to the F/# of the system. Therefore, in general, a low F/# beam delivery optical system is desirable in order to obtain a small focal point in the eye, and therefore maximize the spatial peak irradiance at the focal plane. This allows for a reduction of the laser energy necessary to produce photodisruption, resulting in a smaller shock wave and with smaller zone of collateral damage and less heat transferred to the adjacent tissue. Also, due to the small volume of tissue where photodisruption occurs, a low F/# system allows for high precision cuts with complex patterns.

However, low F/# systems are very susceptible to optical aberrations as the laser beam passes through the optics and the transparent tissue of the eye. Such aberrations alter the spatial irradiance distribution at the focal point, reducing the peak irradiance. Furthermore, in a low F/# system, aberrations vary with the position of the focal point within the eye. For example; in general, the deeper into the tissue the beam is focused, and the further off the axis of the focusing optics the beam is focused, the greater the aberrations. The aberrations are also generally increased significantly when the beam must pass from across curved interfaces between two transparent materials of different refractive indices. Since creating incisions in the cornea and lens requires focusing relatively deep into the tissue, focusing considerably off axis and crossing curved interfaces between transparent materials, it is very challenging to design an optical system capable of focusing a beam over a large three-dimensional working space in the eye using a low F/# beam delivery system while maintaining a relatively unaberrated focal point throughout the entire three-dimensional space.

Currently, there are ophthalmic surgery systems specializing in cutting into the cornea using low F/# beam delivery optical systems, such as the Intralase FS system manufactured and sold by Abbott Medical Optics of Abbott Park, Ill., the VisuMax Femtosecond system manufactured and sold by Carl Zeiss Meditech of Dublin, Calif. and the Technolas Femtosecond Workstation manufactured and sold by Technolas Perfect Vision of München, Germany. However, these systems only cover a limited three-dimensional working space. In particular, although a beam focus must be formed off-axis, the depth of the incisions is limited to no more than the depth of the cornea, about 600 µm. Furthermore, in some of these systems it is required to flatten the cornea in order to eliminate aberrations such as coma and astigmatism that result from the laser beam passing through the curved cornea. No current system has fully addressed the challenging problem of generating a sharp, minimally aberrated beam focus to generate incisions over the full diameter of the cornea and full depth of the cornea and crystalline lens. In other words, no current systems, such as the previously mentioned low F/# beam delivery optical systems, cover any specific method to reduce aberrations while covering a large three-dimensional working space in the eye using a low F/# optical system.

BRIEF SUMMARY

One aspect of the present invention regards a laser system including a laser source that generates a laser beam and an optical switch that receives the laser beam and selectively sends the laser beam to either a fast path or a slow path, wherein in the fast path the laser beam has a first F/# and in the slow path the laser beam has a second F/# that is higher in value that of the first F/#. The laser system further including an afocal optical system that is in the slow path and receives the laser beam from the optical switch and an x-y scanner that receives either a first laser beam from the slow path or a second laser beam from the fast path. The laser system including a scan lens system that receives a scanning laser beam from the x-y scanner and performs a z-scan for the scanning laser beam only in the case wherein the scanning laser beam is generated from the laser beam in the fast path. The laser system further including an aspheric patient interface device that receives a laser beam from the scan lens system.

A second aspect of the present invention regards a method of surgically repairing an eye that includes generating a laser beam and selectively sending the laser beam to either a fast path or a slow path, wherein in the fast path said laser beam has a first F/# and in the slow path the laser beam has a second F/# that is higher in value than that of the first F/#. The method including having an afocal optical system in the slow path and performing an x-y scan of either a first laser beam from the slow path or a second laser beam from the fast path. The method further including having a scan lens system receive a scanning laser beam based on said x-y scanning and perform a z-scan for the scanning laser beam only in the case wherein the scanning laser beam is generated from the laser beam in the fast path. The method further including having an aspheric patient interface device receive a laser beam from the scan lens system, wherein the aspheric patient interface device is in contact with a cornea of an eye and directs the laser beam from the scan lens system to either 1) the cornea only in the case wherein the scanning laser beam is generated from the laser beam in the fast path or 2) a crystalline lens of the eye only in the case wherein the scanning laser beam is generated from the laser beam in the slow path.

A third aspect of the present invention regards a method of reducing aberrations during surgical repair of an eye, the method including positioning an aspherical patient interface device so as to contact a cornea of an eye, wherein the cornea is not flattened during the positioning and the cornea conforms to a shape of a bottom surface of the aspherical patient interface device. The method including directing a laser beam through the aspherical patient interface device to a volume of the eye, wherein the laser beam does not suffer from aberrations when arriving at the volume of the eye.

A fourth aspect of the present invention regards a scan lens system that includes a first lens, a second lens, a third lens and a fourth lens, wherein the first lens, second lens, third lens and the fourth lens are arranged in series with one another. In addition, the second lens and the third lens are each positioned between the first lens and the fourth lens and wherein the second lens and the third lens are stationary with respect to each other and the first and fourth lenses can move in unison relative to the second lens and the third lens.

A fifth aspect of the present invention regards an afocal system that includes a first negative lens, a second negative lens, a first positive lens and a second positive lens, wherein the first positive lens, the second positive lens, the first negative lens and the second negative lens are in series with one another. In addition, the first positive lens and the second positive lens are fixed in position while the first negative lens and the second negative lens move in unison to one another relative to the first positive lens and the second positive lens.

A sixth aspect of the present invention regards a laser system that includes a laser source that generates a laser beam along a fast path, wherein the laser beam in the fast path has a F/# having a value ranging from F/1.5 to F/4. The laser system further including an aspheric patient interface device that receives the laser beam from the laser source, wherein the aspheric patient interface device is in contact with a cornea of an eye and directs the laser beam to the cornea.

A seventh aspect of the present invention regards a laser system that includes a laser source that generates a laser beam along a path and an afocal optical system that is in the path and receives the laser beam from the laser source and an F/# varying element that is in the path and changes the laser beam so that it has either a first F/# value or a second F/# value. The laser system includes an x-y scanner that receives the changed laser beam having either the first F/# value or the second F/# value and a scan lens system that receives a scanning laser beam from the x-y scanner and performs a z-scan for the scanning laser beam only in the case wherein the changed laser beam has the first F/# value. The laser system further including an aspheric patient interface device that receives a laser beam from the scan lens system.

An eighth aspect of the present invention regards an ophthalmic laser system including a laser source that generates a laser beam and an optical switch that receives the laser beam and selectively sends the laser beam to either a fast path or a slow path, wherein in the fast path the laser beam has a first F/# and in the slow path the laser beam has a second F/# that is higher in value than the first F/#. The ophthalmic laser system including an adaptive optic device that is in the fast path and an x-y-z translation device that receives either a first laser beam from the slow path or a second laser beam from the fast path. The ophthalmic laser system further including a rotating optical system that receives a laser beam from the x-y-z translation device and performs a partial or full circular scan of the received laser beam about an axis of rotation of the rotating optical system, wherein the rotating optical system is able to translate so as to vary a radius of the partial or full circular scan and the partial or full circular scan is positioned in an eye of a patient. In addition, the adaptive optic corrects the laser beam received form the fast path so that aberrations at the partial or full circular scan are significantly reduced.

A ninth aspect of the present invention regards an ophthalmic laser system that includes a laser source that generates a laser beam and an optical switch that receives the laser beam and selectively transforms the laser beam to either a fast path laser beam or a slow path laser beam, wherein the fast path laser beam has a first F/# and the slow path laser beam has a second F/# that is higher in value than first F/#. An adaptive optic device receives either the fast path laser beam or the slow path laser beam from the optical switch. An x-y-z translation device that receives either the fast path laser beam or the slow path laser beam from the adaptive optic. The ophthalmic laser system further including a rotating optical system that receives a laser beam from the x-y-z translation device and performs a partial or full circular scan of the received laser beam about an axis of rotation of the rotating optical system, wherein the rotating optical system is able to translate so as to vary a radius of the partial or full circular scan and the partial or full circular scan is positioned in an eye of a patient. In addition, the adaptive optic corrects the fast laser beam so that aberrations along the partial or full circular scan are significantly reduced.

A tenth aspect of the present invention regards a method of surgically repairing an eye that includes generating a laser beam and selectively manipulating the laser beam so that the laser beam is present in either a fast path or a slow path, wherein in the fast path the laser beam has a first F/# and in the slow path said laser beam has a second F/# that is higher in value than the first F/#. The method includes having an adaptive optic device that is in the fast path to receive the selectively sent laser beam in the fast path and having an x-y-z translation device that receives either the fast path laser beam or the slow path laser beam from the adaptive optic. The method further includes receiving a laser beam from the x-y-z translation device and performing a partial or full circular scan of the received laser beam and varying a radius of the partial or full circular scan, wherein the partial or full circular scan is positioned in an eye of a patient. In addition, the adaptive optic corrects the laser beam received from the fast path so that aberrations along the partial or full circular scan are significantly reduced.

An eleventh aspect of the present invention regards a rotating optical system that includes a housing that rotates about an axis of rotation, wherein the housing has a window to receive a laser beam. The rotating optical system includes a translating stage that is present within the housing and translates relative to the housing, the translating stage having a lens. The rotating optical system further including an optical system for directing the laser beam from the window to the lens, wherein the lens directs the laser beam to a focal point exterior of the housing.

A twelfth aspect of the present invention regards an adaptive optic that includes a beam splitting device that has an input side for receiving light and an output side for transmitting light. The adaptive optic further including a deformable mirror that receives the received light from the input side and directs the received light to the output side.

One or more aspects of the present invention allow for a reduction in the complexity of optics in an ophthalmic beam delivery optical system. Another advantage of this present invention is that the adaptive optic device allows for significant flexibility in correcting various aberrations that may occur in the laser beam.

One or more aspects of the present invention allow for a reduction in the complexity of optics and the number of moving elements in a beam delivery optical system.

BRIEF DESCRIPTION OF THE DRAWING

The accompanying drawings, which are incorporated herein and constitute part of this specification, and, together with the general description given above and the detailed description given below, serve to explain features of the present invention. In the drawings:

FIG. 17A schematically shows crystalline lens fragmentation cuts that include transversal arc-shaped cuts and circular cuts, which are done with the slow laser beam (large F/#);

FIG. 17B shows a typical example of a circular path described by the laser focus when cutting transversal arc-shaped cuts during the fragmentation of a crystalline lens;

DETAILED DESCRIPTION OF THE PREFERRED EMBODIMENTS

Figure 1:
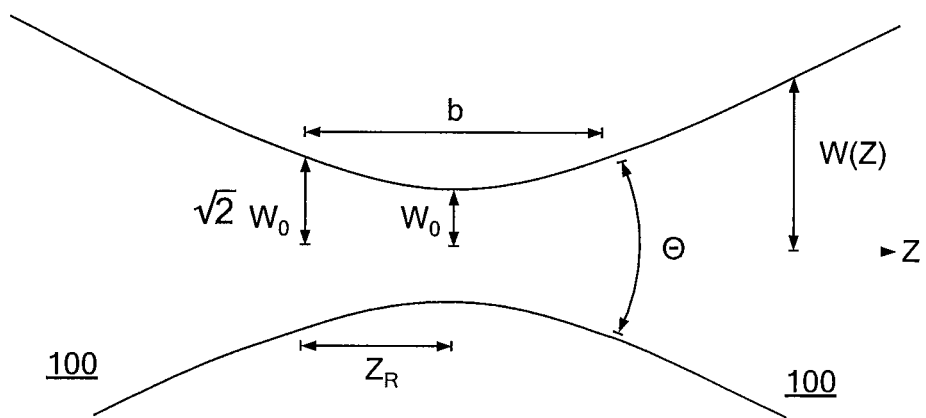
FIG. 1 schematically shows a Gaussian beam that shows various parameters of a beam.
Figure 2:
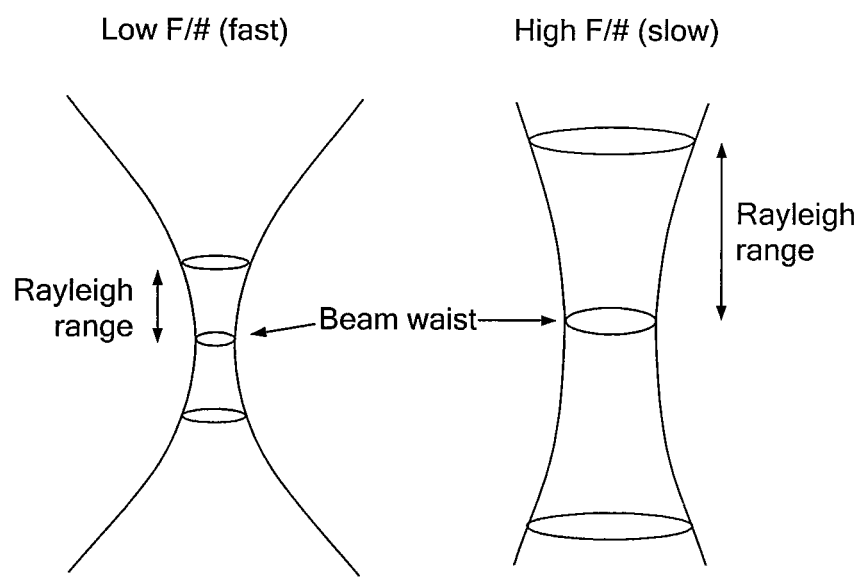
FIG. 2 schematically compares beam waist and Rayleigh range values for low F/# and high F/# beams.

Note that in order to understand some of the properties of the present invention, FIG. 1 is presented which schematically shows a beam, such as a Gaussian beam 100. The beam waist $W_0$ and Rayleigh range $Z_R$ are two key parameters that determine how localized the photodisruption and additional thermal effects will be around the focal point of the beam. The beam waist is directly proportional to the beam F/#, so the peak spatial irradiance at the waist is inversely proportional to the square of the F/#. The Rayleigh range of a Gaussian beam is defined as the distance along the laser beam (Z-axis) from the beam waist to the point where the beam expands by sqrt(2), and is directly proportional to the square of the beam waist. Therefore, the Rayleigh range is inversely proportional to the square of the F/#. Note that at one Rayleigh range away from the waist, the peak irradiance will drop in half compared to the peak irradiance at the waist. With the above said, the Rayleigh range and waist for a high F/# beam will be larger than the Rayleigh range for a low F/# beam as shown in FIG. 2.

Figure 3:
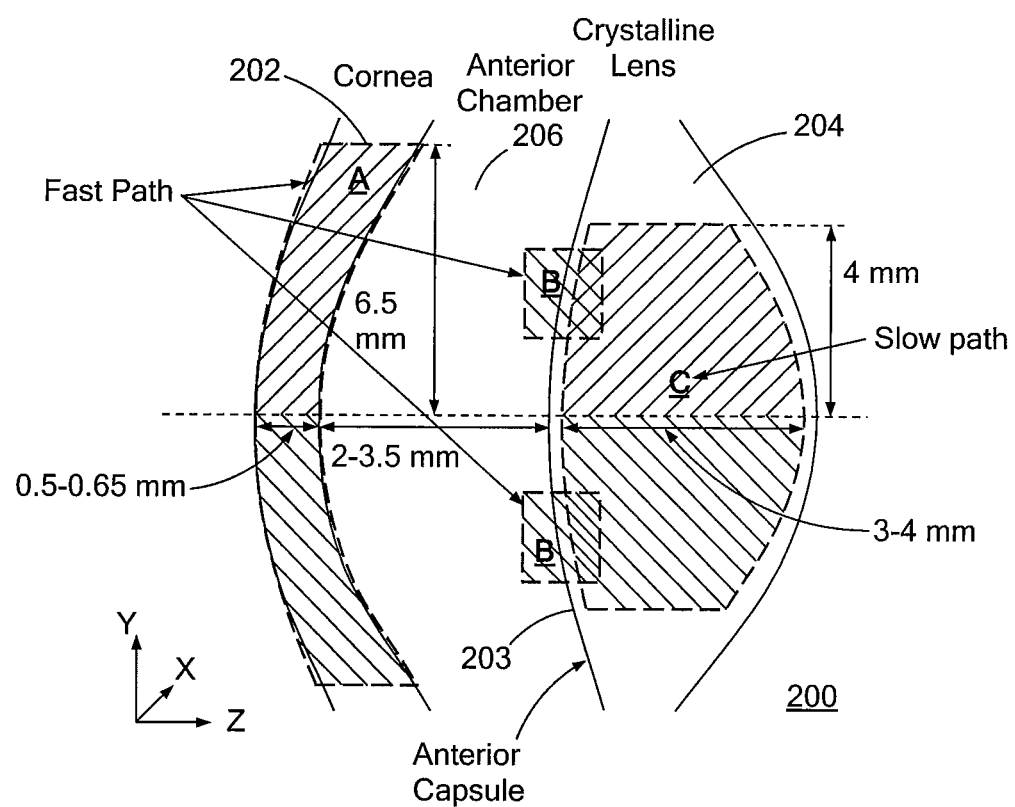
FIG. 3 schematically shows a cross-section of an eye.

As shown by the shaded areas of FIG. 3, there are two areas of interest regarding the formation of incisions or cuts in an eye 200—the cornea 202 and the crystalline lens 204. In the case of cuts formed in the three-dimensional working space A (see hashed line area of cornea 202 of FIG. 3) in the cornea 202, it is desirable to reduce the Rayleigh range and waist of the laser beam, as high precision and the ability to cut complex patterns within a very small volume are critical factors in cutting the cornea (Clear Corneal Incisions—CCIs, Limbal Relaxation Incisions—LRIs, flaps). A shorter Rayleigh range reduces the depth of the cut formed by a single laser pulse on the Z-axis, increasing the accuracy of placing LRI cuts in terms of length and location on Z. The accuracy of LRIs in Z is important so that LRIs could be placed relatively close to the endothelium without the risk of completely cutting through the cornea into the anterior chamber. In the case of CCIs, a shorter Rayleigh range allows cutting more complex and precise patterns as viewed in the cross-section formed by a plane containing the Z-axis. Such patterns are beneficial as they help sealing the CCI after the cataract surgery. In addition, with a shorter Rayleigh range the beam irradiance decreases faster with Z from the beam waist, which allows cutting into the corneal stroma without damaging the epithelium or endothelium due to thermal effects. Based on the above advantages of using a beam of a shorter Rayleigh range, low F/# beams are preferred for forming cuts in the cornea 202.

In the case of cuts formed in the three-dimensional working spaces B (see hashed line areas in the vicinity of the anterior capsule 203 of the crystalline lens 204 of FIG. 3) in the vicinity of the anterior capsule 203 of the crystalline lens 204 during a capsulotomy, it is desirable to reduce the Rayleigh range and waist of the laser beam in order to minimize the potential collateral damage to the area of the anterior capsule that is in close proximity to the capsulotomy cut. In a typical capsulotomy performed with a laser beam, laser pulses are directed in a cylindrical pattern (of diameter equal to the desired capsulotomy diameter), starting in the crystalline lens 204, posterior to the anterior capsule 203, and moving upwards through the anterior capsule 203, towards the anterior chamber 206. A shorter Rayleigh range and a smaller laser beam waist ensure that when the laser beam waist is focused posterior or anterior to the anterior capsule 203, less energy density falls onto the area of the anterior capsule that is in close proximity to the capsulotomy cut, which preserves the elasticity of the capsule around the cut, therefore improving the strength of the capsule around the cut. A smaller laser beam waist also allows for less laser energy to be used for capsulotomy, and ensures a cleaner cut, further improving the strength of the anterior capsule 203 around the cut. A strong capsule tissue around the capsulotomy reduces the possibility of unwanted tears in the anterior capsule 203 during the capsulorhexis, improving the precision of placing the intra-ocular lens during a cataract surgery, which is one of the critical factors in the outcome of the surgery. Based on the above advantages of using a beam of a shorter Rayleigh range and smaller waist, low F/# beams are preferred for forming cuts in the anterior capsule 203.

When cutting the three-dimensional working space C (see hashed line area of crystalline lens 204 of FIG. 3) of crystalline lens 204, the laser beam passes through more tissue with variable or unknown properties than in the case of the corneal cuts. This results in less predictable refractions of the beam and therefore less predictable aberrations, which could not be accounted for in the optical design, and therefore would remain uncorrected. Therefore, in the case of the crystalline lens cuts or incisions (fragmentation and capsulotomy) performed in general or, in particular, performed in space C it is desirable to use a high F/# beam, because such a beam is less sensitive to the aberrations introduced by the patient-to-patient variations in the eye geometry (anterior chamber depth, thicknesses and radii of curvature of the cornea and crystalline lens) and the refractive index of the crystalline lens 204.

Also, due to the less complex nature of the typical cutting patterns for the fragmentation and capsulotomy, the precision required is relatively lower compared to the precision required for the corneal cuts. Corneal cuts need to have the depth (on Z-axis) controlled to a few tens of microns or about 5% of the thickness of the cornea 202; crystalline lens cuts need to have a z control in the range of a couple of hundred microns or about 5% of the thickness of the crystalline lens 204.

Figure 4:
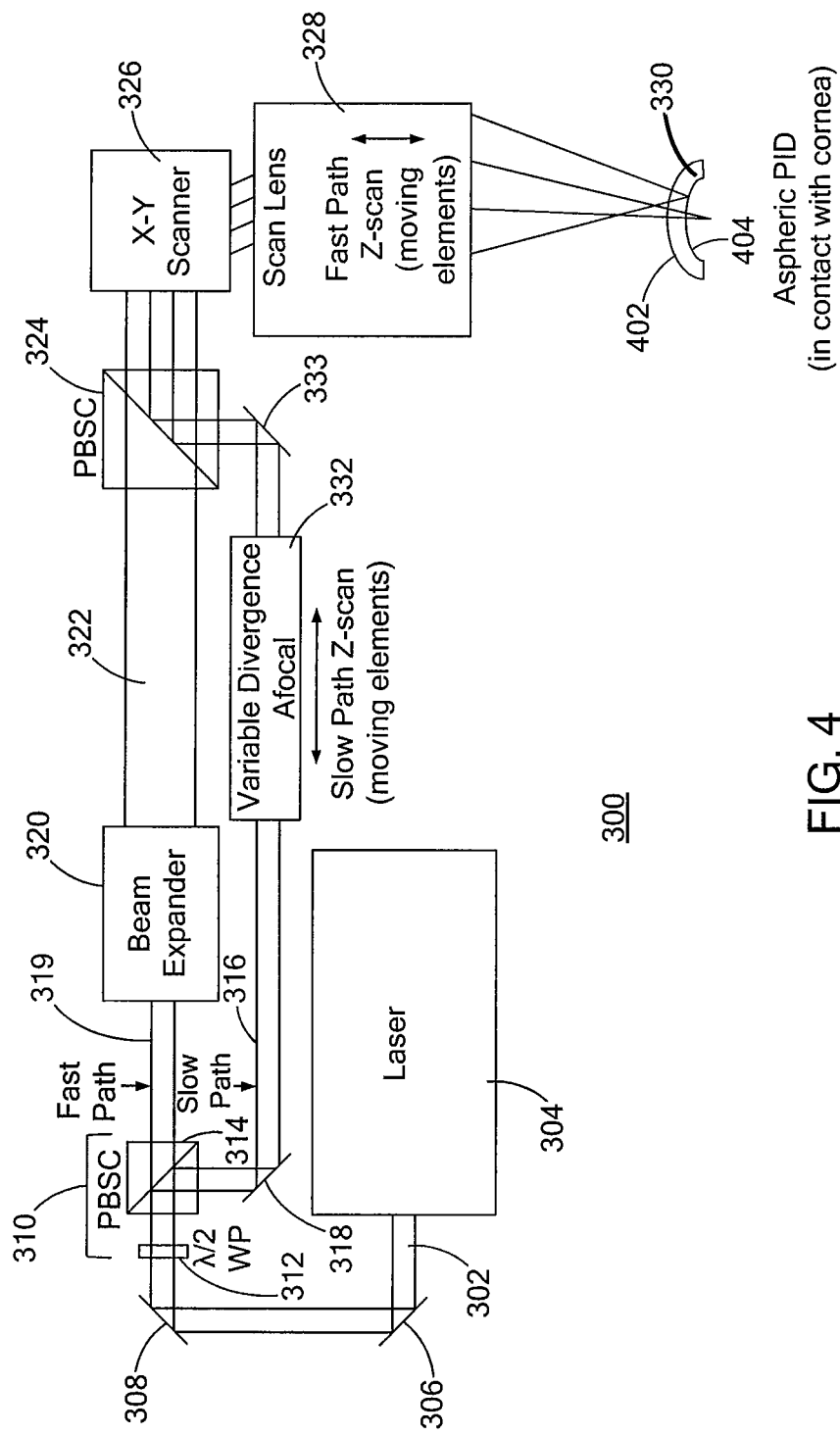
FIG. 4 schematically shows a first embodiment of a beam delivery optical system in accordance with the present invention.

With the above discussion regarding the desire to form cuts in the cornea 202 with a low F/# beam and form cuts in the crystalline lens 204 with a high F/# beam, an embodiment of a beam delivery optical system 300 that can form cuts with both types of beams is illustrated in FIG. 4. In particular, a laser beam 302 is generated by a laser source 304 and directed via mirrors 306, 308 to an optical switch 310. The optical switch 310 includes a $\lambda/2$ wave plate 312 and a polarization beam splitter cube (PBSC) 314. Rotating a $\lambda/2$ wave plate by a certain angle rotates the polarization of an incident linearly polarized beam by double the said angle, so the $\lambda/2$ wave plate 312 in the optical switch 310 acts as a polarization rotator. A PBSC reflects all light with the polarization parallel to the plane of its reflective surface and transmits all light with the polarization 90 degrees rotated with respect to the reflected polarization. With the above said, as the laser beam 302 is linearly polarized, rotating the $\lambda/2$ wave plate 312 in a first position allows the laser beam 302 to pass entirely through the PBSC 314 to travel along a fast path 319 and not a slow path 316 of the system 300. Rotating the $\lambda/2$ wave plate 312 by 45 degrees with respect to the first position allows the laser beam 302 to be entirely reflected by the PBSC 314 and directed to a mirror 318 so that the laser beam 302 travels along the slow path 316 and not the fast path 319. Thus, the optical switch 310 switches the laser beam 302 between the fast path 319 and the slow path 316, wherein only one path at a time is used during cutting. While the $\lambda/2$ wave plate 312 rotates by 45 degrees to switch between the slow path 316 and the fast path 319, the laser will be shut off. So, it will be a short delay during which the laser beam will be "off" allowing to completely switch between the two paths In the fast path 319, the laser beam 302 is expanded by a beam expander 320 with a magnification equal to the ratio between the F/# of the beam directed along the slow path 316 and the F/# of the laser beam directed along the fast path 319. The expansion of the beam is equivalent to expanding the entrance pupil diameter D and so the F/# is reduced. Thus, beam expander 320 acts as an F/# varying element. Note that the particular magnification for beam expander 320 is chosen in view of the fact that the beam in the slow path is not expanded. The expanded laser beam 322 is then directed through a second PBSC 324 and passed on to an x-y scanner 326. The x-y scanner 326 is used to direct the light through a scan lens to particular areas of the eye in a well known manner. The light from the x-y scanner is focused through a scan lens system 328, which focuses the scanning laser beam through the aspheric patient interface device 330 into the eye. After passing through the scan lens system 328, the light is then directed to an aspheric patient interface device 330 that is in contact with the cornea 202 of the eye 200 that is being surgically repaired. The laser beam is then directed to the cornea 202 wherein incisions or cuts are made thereto pursuant to a predetermined pattern. The details regarding the beam expander 320, the scan lens system 328 and the aspheric patient interface device 330 will be explained later in the present application.

When the optical switch 310 directs light along the slow path 316, the laser beam goes through a z-scanning afocal optical system 332 with variable output beam divergence. The magnification of the afocal system 332 is 1 when the output beam divergence is at its minimum value. The use of such an afocal optical system 332 in the slow path 316 is needed to achieve scanning in a vertical axis of the eye 200 (defined here as Z-axis) by varying the divergence of the laser beam as will be discussed later. As shown in FIG. 4, the fast path 319 and the slow path 316 (via mirror 333) are recombined by the second polarization beam splitter cube (PBSC) 324 and both sent into the horizontal x-y scanner 326.

Note that the operation of PBSCs 314 and 324 is such that all light reflected by PBSC 314 into the slow path will be reflected by PBSC 324 back onto the optical axis of the x-y scanner/scan lens due to the polarization being parallel to the reflecting surface of both PSCs. Likewise, all light transmitted by PBSC 314 will be transmitted by PBSC 324. The advantage of using PBSCs is that the power loss is minimized through the system since they transmit or reflect all light.

In the case of the slow path 316 and the laser beam leaving PBSC 324 and sent to scanner 326, the laser beam from the scanner 326 is then sent to scan lens system 328. When the beam is delivered through the slow path 316, all elements within the scan lens system 328 are fixed and configured to generate the deepest cut. The low F/# scanning laser beam 334 from scan lens system 328 is then directed through the aspheric patient interface device 330 to the crystalline lens 204 wherein incisions or cuts are made thereto pursuant to a predetermined pattern. The details regarding the z-scanning afocal optical system 332 will be explained later in the present application.

Figure 5:
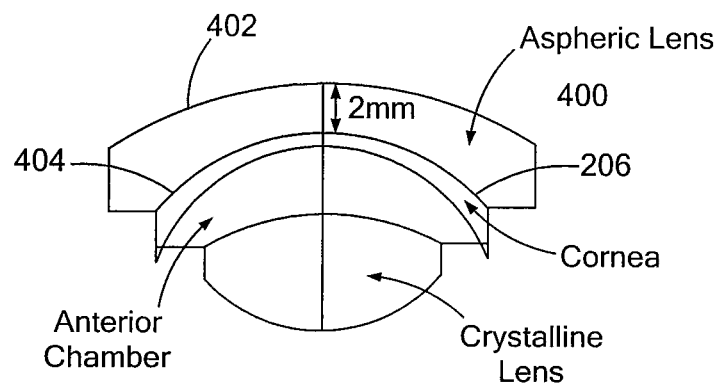
FIG. 5 schematically shows and embodiment of an aspheric lens to be used with the beam delivery optical system of FIG. 4 in accordance with the present invention.

An example of the aspheric interface device 330 used in the beam delivery optical system 300 of FIG. 4 is shown in FIG. 5. In particular, a meniscus aspheric precision glass molded lens 400 can be used for device 330 and is placed in contact with the anterior surface 206 of the cornea 202. Note that the device 330 should be positioned initially to barely touch the cornea at the center wherein x-y adjustment is made if necessary. Once centered, suction is applied to lift up the limbus until it contacts the lens 400. The lens 400 is preferably manufactured by a precision glass molding process, which is a very well suited fabrication method for high-volume production when precision is an important factor. The lens 400 can be molded directly into a metal holder, or a plastic holder can be injection-molded around the lens after the lens is molded. Such manufacturing processes are known to be performed by several manufacturers, such as LightPath of Orlando, Fla. and RPO—Rochester Precision Optics of Rochester, N.Y. The lens 400 can have the following properties: 1) 2 mm center thickness, 2) meniscus shaped, 3) BK-7 glass and 4) 18 mm diameter. Other moldable glasses, including radiation-hardened glasses, such as Ce-doped glasses, can be used for lens 400. Note that the dimensions and type of glass can be varied without departing from the spirit of the invention.

The top (convex) surface 402 of the lens 400 is aspheric and described by an even-aspheric equation. The bottom surface 404 of the lens 400 is also aspheric and described by a conic equation. This lens 400 allows for precise positioning of the cornea 202 with respect to the rest of the beam delivery optics (centration, tilt, depth), and will also provide a fixed and known shape of the anterior surface of the cornea 202 during the formation of the surgical cuts. The range of anterior corneal radii is about 7.00-8.65 mm with an approximate conic constant K=−0.2. The cornea 202 is not flattened, but rather conformed to a surface with a slightly larger radius and a similar conic (for example: R=9 mm, K=−0.2). The conic shape of the portion of the bottom surface 404 in contact with the cornea 202 emulates the natural slight increase in radius of the cornea 202 towards the limbus, and, thus, decreases the possibility of folds in the cornea 202 or air being trapped between the glass lens 400 and cornea 202. Another very important advantage of this interface is the ability to use the anterior aspheric surface 402 of the molded lens 400 (air-glass interface) as a "field lens." Since this aspheric surface 402 is so close to the working space in the cornea 202, it can be used very effectively in combination with the scan lens system 328 to reduce aberrations like astigmatism and coma when cutting the cornea 202 with a low F/# laser beam 336 at different radial positions and different depths. In addition, a low F/# laser beam can be generated and sent directly to lens 400 that is in contact with the cornea of the eye. The lens 400 by itself reduces the effect of aberrations when cutting the cornea 202 with the low F/# laser beam.

Figure 6:
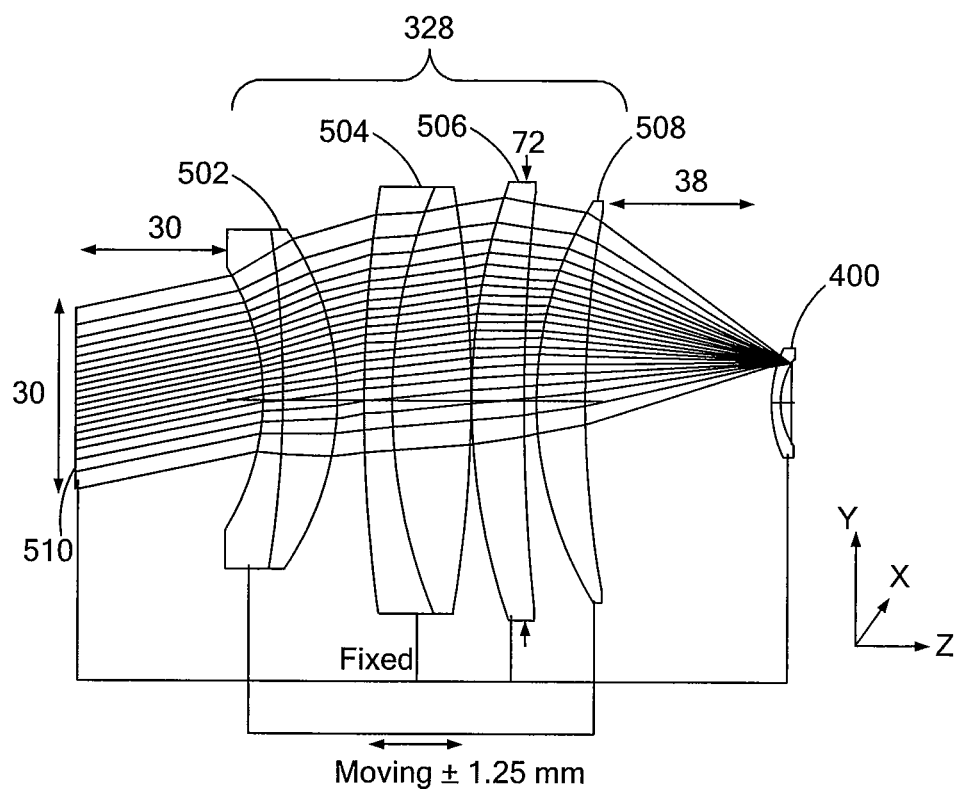
FIG. 6 schematically shows an embodiment of a scan lens system to be used with the beam delivery optical system of FIG. 4 in accordance with the present invention.

Regarding the scan lens system 328, an embodiment is shown in FIG. 6. In particular, the scan lens system 328 includes four lenses 502, 504, 506 and 508 contained in a lens mechanical housing (not shown). The middle lenses 504 and 506 are stationary with respect to each other and the housing, and are separated from one another by approximately 0.5 mm. The outer lenses 502 and 508 are a distance of approximately 46 mm from each other and are able to translate in unison by a total amount of approximately 2.5 mm. The distance between lens 502 and lens 504 varies between 9 mm and 6.5 mm as lenses 502 and 508 are moving together by approximately 2.5 mm to achieve the z-scanning for the low F/# laser beam. As shown in FIG. 6, the edge of the rear surface of lens 508 is approximately 38 mm from the front surface 402 of lens 400. In addition, the edge of the front surface of the lens 502 is approximately 30 mm away from the entrance pupil 510 of the scan lens system 328, which allows placing the center of rotation of an X-Y scanner 326 with a 30 mm aperture at the entrance pupil of the scan lens system 328.

Note that lens 502 is a cemented doublet with negative power (focal length of approximately −250 mm) formed by a negative meniscus lens with a center thickness of approximately 5 mm cemented to a positive meniscus lens with a center thickness of approximately 12 mm. Lens 504 is a cemented doublet with positive power (focal length of approximately 270 mm) formed by a negative meniscus lens with a center thickness of approximately 6 mm cemented to a positive bi-convex lens with a center thickness of approximately 18 mm. Lens 506 is a meniscus shaped singlet with positive power (focal length of approximately 150 mm) with a center thickness of approximately 12 mm. Lens 508 is a meniscus shaped singlet with positive power (focal length of approximately 100 mm) with a center thickness of approximately 11 mm. All diameters of lenses 502, 504, 506, and 508 are smaller than approximately 72 mm.

In operation, scan lens system 328 has an effective focal length of approximately 45 mm and an entrance pupil 510 of approximately 30 mm. When receiving the laser beam from the fast path, the scan lens system 328 is capable of delivering an F/1.5 laser beam into the cornea 202 while covering the full three-dimensional working space A in the cornea 202 as defined in FIG. 3 (13 mm maximum cut diameter), and maintaining a Strehl-Ratio larger than approximately 0.8 (the Strehl-Ratio is defined as the spatial peak irradiance of the aberrated focal spot relative to the peak irradiance of an aberration-free spot). During surgery, the x-y scanner 326, the scan lens system 328, and patient interface device 330 are fixed with respect to one another. The vertical scanning (on the Z-axis) for the laser beam from the fast path is performed by the scan lens system 328 by moving axially along the Z axis the front and back lenses 502 and 508 together (as a common body). While the lenses 502 and 508 move, the lenses 504 and 506 are fixed with respect to the lens mechanical mount. Note that the lens scan system 328 can include an actuator (motor) onto which lenses 502 and 508 would be mounted together. The motor would be mounted on the scan lens system 328, which is fixed with respect to the eye 200 and with respect to the x-y scanner 326. In the case of a laser beam received from the fast path, the combination of this axial movement of lenses 502 and 508 in the scan lens system 328, x-y scanning angle, and the aspheric lens 400 used as the patient interface device 330 allows placing the focused beam waist at different points in the required three-dimensional working space A in the cornea. In addition, it is very important to note that this scanning combined with the aspheric patient interface 330 automatically corrects the aberrations that vary with the position of the focal point within the cornea 202.

Figure 7A:
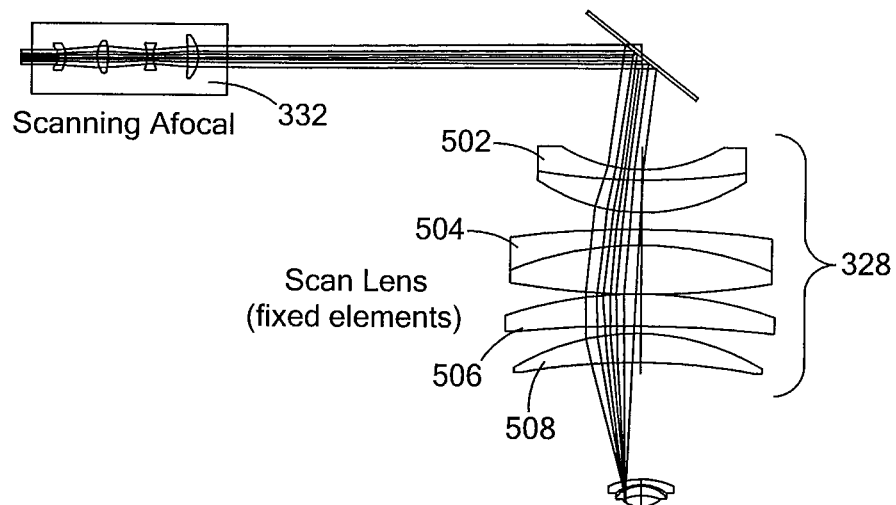
FIG. 7A schematically shows an embodiment of a z-scan afocal system to be used with the beam delivery optical system of FIG. 4 in accordance with the present invention.
Figure 7B:
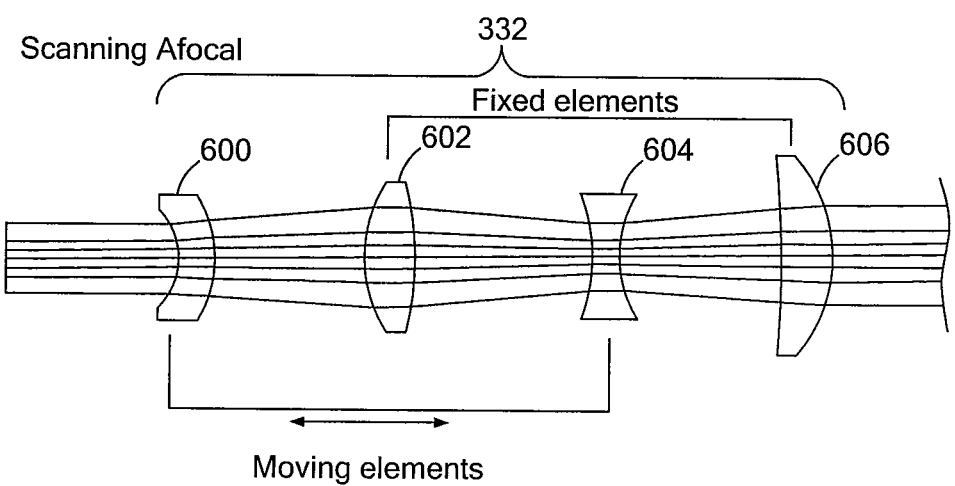
FIG. 7B shows an enlarged view of the afocal system of FIG. 7A.

On the slow path, the system delivers an F/4 beam into the crystalline lens working space B as defined in FIG. 3. In the slow path configuration, the moving elements within the scan lens system 328 remain fixed in the position corresponding to the deepest corneal cut, while the scanning on the Z-axis is done by varying the divergence of the beam generated by the afocal system 332. The optical arrangement for the afocal system 332 that performs the Z-scanning for a beam in the slow path 316 is shown in FIGS. 7A-B. As shown in FIG. 7B, system, the afocal system 332 includes negative lenses 600 and 604 and positive lenses 602 and 606. The lenses 602 and 606 are fixed to a mechanical housing so as to be a distance of 21 mm from one another.

Note that lens 600 is a negative meniscus singlet with a focal length of approximately −30 mm and a center thickness of approximately 2 mm. Lens 602 is a positive bi-convex singlet with a focal length of approximately 20 mm and a center thickness of approximately 3 mm. Lens 604 is a negative bi-concave singlet with a focal length of approximately −10 mm and a center thickness of approximately 1.5 mm. Lens 606 is a positive meniscus singlet with a focal length of approximately 35 mm and a center thickness of approximately 3 mm. The spacing between lens 600 and lens 602 is approximately 9 mm. The lenses 600 and 604 move in unison with each other with respect to the lenses 602 and 606 by a total displacement of approximately 6 mm. The particular arrangement and relative motion of lenses 600, 602, 604 and 606 form an optical zoom configuration that allows placing the z-scanning afocal system 332 further away from the scan lens system 328 (when compared with known configurations for z-scanning afocal systems that include the commercially available two-element Galilean telescope embodiment that includes a negative element followed by a positive element, where the negative element is moved with respect to the positive element) while still maintaining a constant F/# at the image plane over the full Z scan range. Placing the afocal system 332 further away from the scan lens system 328 is beneficial due to various mechanical constraints, like the size of the second PBSC 324 and the size of the x-y scanner 326. The optical zooming helps with the increased spacing from the scan lens system 328 in that while divergence increases, the output beam from the afocal system 332 decreases to keep the beam diameter at the input of the scan lens system 328 somewhat constant. That way, the F/# of the beam coming out of the scan lens stays constant while scanning on Z.

Note that other embodiments for a dual beam delivery optical system are possible. An example of such an optical system is the beam delivery optical system 700 shown in FIG. 8. The structure of beam delivery optical system 700 is similar to beam delivery optical system 300 of FIG. 4. In particular, a laser beam 302 is generated by a laser source 304 and directed via mirrors 306, 308 to an optical switch 310. In contrast to the λ/2 wave plate 312 and polarization beam splitter cube (PBSC) 314 of FIG. 4, the system 700 uses a turning mirror 702 that can rotate to a first position so that the laser beam 302 is directed to mirror 318 and the slow path so that it can be processed by afocal system 332 in a manner as described with respect to the embodiment of FIG. 4. Rotating turning mirror 702 causes the laser beam 302 to reflect off of mirror 704 and directed to the fast path to be processed by the beam expander 320 in a manner as described with respect to the embodiment of FIG. 4.

Figure 8:
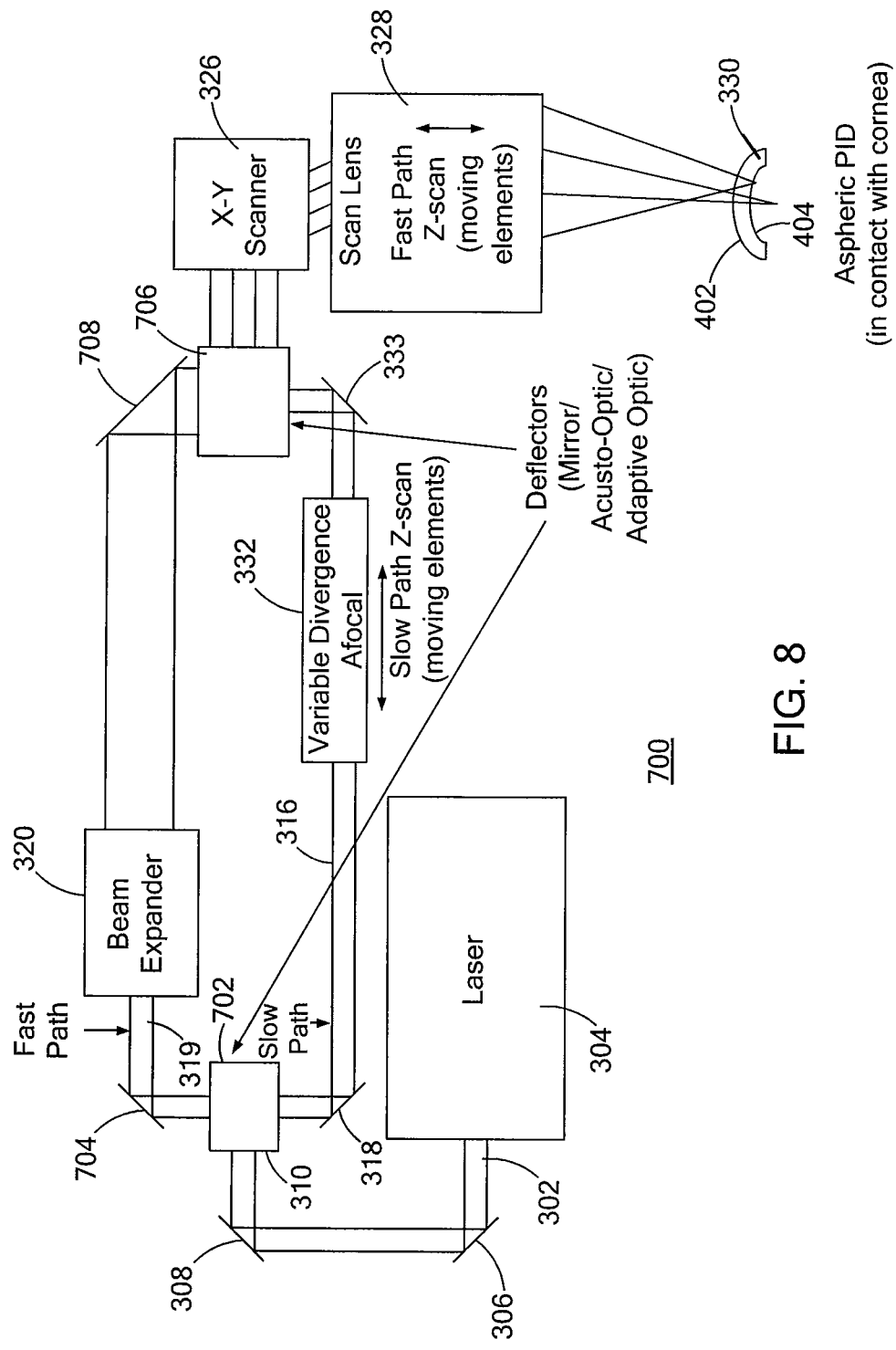
FIG. 8 schematically shows a second embodiment of a beam delivery optical system in accordance with the present invention.

As shown in FIG. 8, the fast path laser beam is deflected by a mirror 708 to a second turning mirror 706 which is positioned at a first position to reflect the fast path laser beam to the x-y scanner 326. Similarly, the slow path laser beam is deflected by a mirror 333 to the turning mirror 706 which is positioned at a second position to reflect the slow path laser beam to the x-y scanner 326. The slow path and fast path laser beams are processed and scanned by the afocal system 332, x-y scanner 326, scan lens 328 and aspheric patient interface device 330 in a manner similar to that described with respect to the embodiment of FIG. 4.

Note that in operation, the rotation of mirrors 702 and 706 are synchronized so that the laser beam 302 passes through either only the fast path 319 or the slow path 316. In addition, the laser beam 302 is stopped or the laser 304 is shut off during rotation of the mirrors 702 and 706.

Other possibilities for the optical switch 310 of FIG. 8 are possible. For example, the mirrors 702 and 706 can be replaced by acusto-opto deflectors, adaptive optics deflectors or regular beam splitters (50/50 splitters, for example). In the case of using regular beam splitters, portions of the laser beam 302 will be present in both the fast path 319 and the slow path 316. Shutters are present in each of the fast and slow paths so that one is closed at any moment of time, the laser beam will travel in the path that is not closed.

Figure 9:
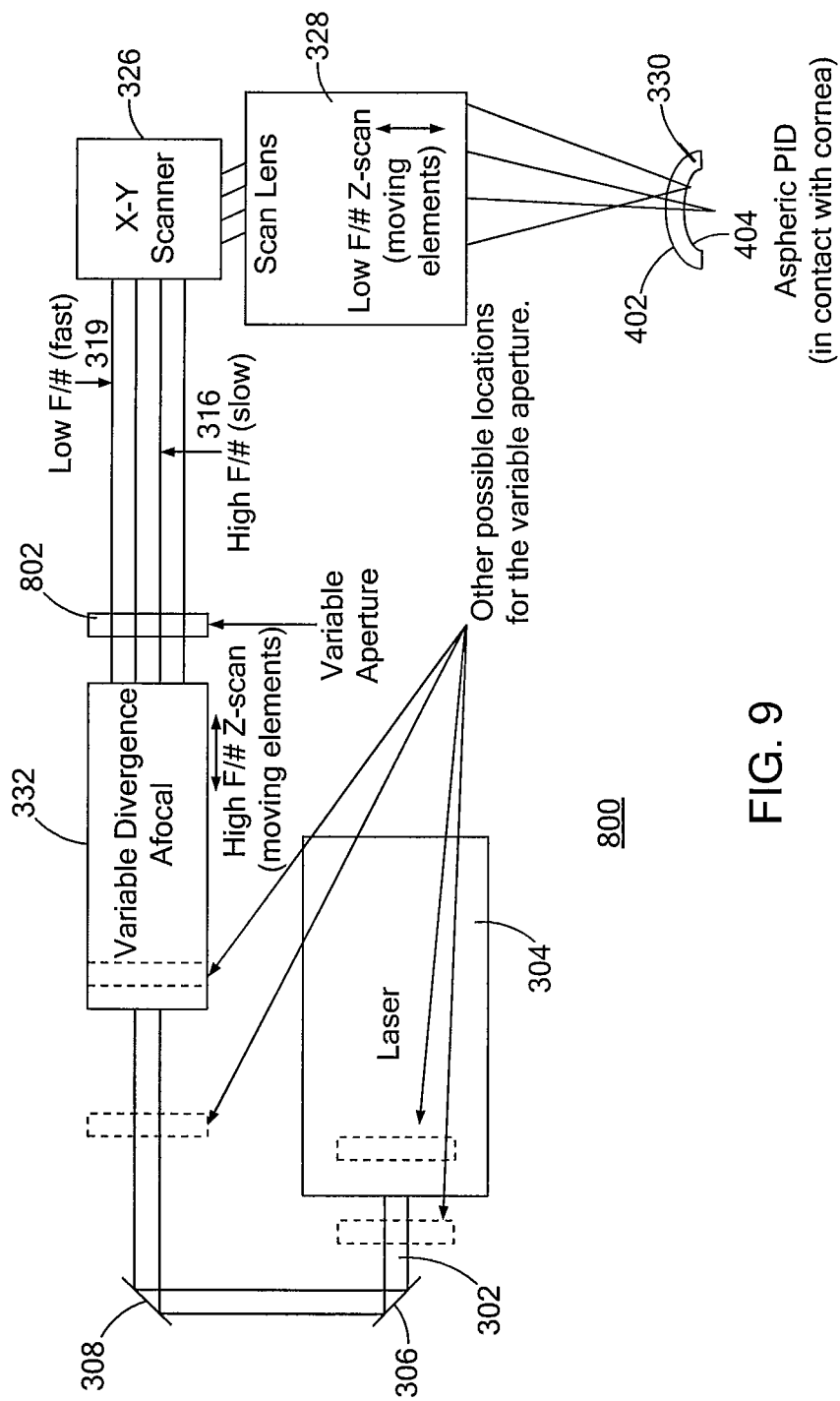
FIG. 9 schematically shows a third embodiment of a beam delivery optical system in accordance with the present invention.
Figure 10:
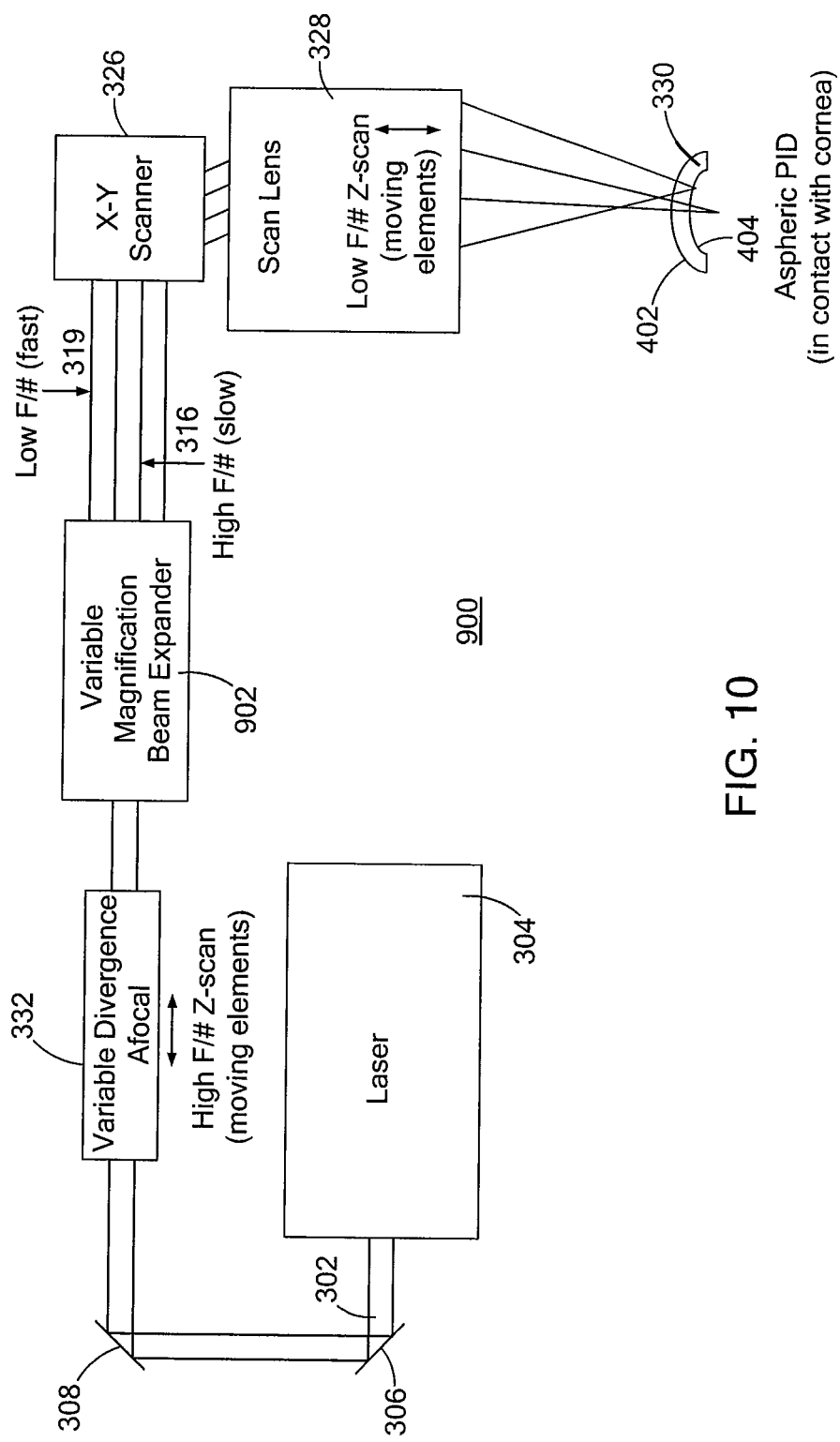
FIG. 10 schematically shows a fourth embodiment of a beam delivery optical system in accordance with the present invention.

The previously described systems 300 and 700 of FIGS. 4 and 8 operated on the principle of separating the fast and slow laser beams in separate paths. As shown in FIGS. 9 and 10, it is possible to generate fast and slow laser beams on a common path. Regarding the embodiment shown in FIG. 9, a beam delivery optical system 800 includes a laser beam 302 that is generated by a laser source 304 and directed via mirrors 306, 308 to a variable divergence afocal system 332. As shown in FIG. 9, the laser beam 302 is transformed by a variable aperture 802 that can be positioned at various locations along the single path. In operation, the variable aperture 802 is controlled to have a first aperture size that will generate a laser beam with a F/# that has a value that is similar to the laser beam present in the slow paths of the systems 300 and 700 of FIGS. 4 and 7. The variable aperture 802 can also be controlled to have a second aperture size that will generate a laser beam with a F/# that has a value that is similar to the laser beam present in the fast paths of the systems 300 and 700 of FIGS. 4 and 7. After the particular laser beam (fast or slow) is formed, it passes through the x-y scanner 326, scan lens 328 and aspheric patient interface device 330 in a manner similar as described previously with respect to systems 300 and 700 of FIGS. 4 and 7. The fast and slow beams are scanned in the z-direction by the scan lens 328 and afocal system 332, respectively, in the manner described previously with respect to FIGS. 4 and 7.

Note that in the alternate embodiment of FIG. 10, a beam delivery optical system 900 is identical to that of system 800 of FIG. 9 wherein variable aperture 802 is replaced by a variable magnification beam expander 902, such as the Motorized Zoom Beam Expander Models VIS-NIR 56C-30-1-4x-λ and 2-8X-λ, manufactured and sold by Special Optics of Wharton, N.J. Instead of varying an aperture size to generate different F/# laser beams as in FIG. 9, the beam expander 902 changes the magnification of the laser beam so as to have different F/# values. Thus, system 900 operates in a manner similar to that of system 800.

Figure 11:
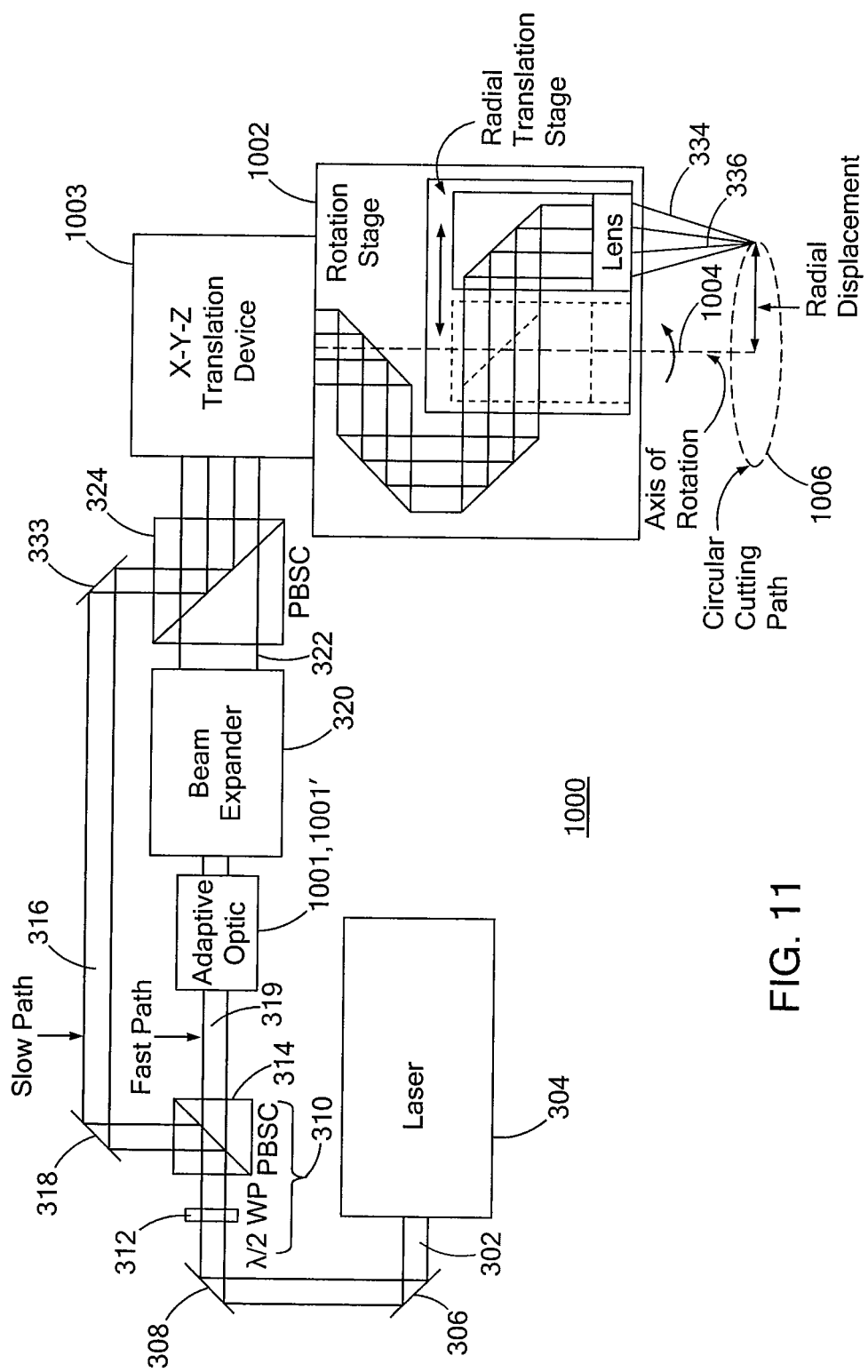
FIG. 11 schematically shows a fifth embodiment of a beam delivery optical system in accordance with the present invention.

An embodiment of a beam delivery optical system 1000 that can form cuts in the cornea 202, anterior capsule 203 and crystalline lens 204 with both low F/# (forming cuts in cornea 202 and anterior capsule 203) and high F/# (forming cuts in crystalline lens 204) types of beams is illustrated in FIG. 11. In particular, a laser beam 302 is generated by a laser source 304 and directed via mirrors 306, 308 to an optical switch 310. The optical switch 310 includes a λ/2 wave plate 312 and a polarization beam splitter cube (PBSC) 314. Rotating a λ/2 wave plate by a certain angle rotates the polarization of an incident linearly polarized beam by double the certain angle, so the λ/2 wave plate 312 in the optical switch 310 acts as a polarization rotator. A PBSC reflects all light with the polarization parallel to the plane of the PBSC's reflective surface and transmits all light with the polarization 90 degrees rotated with respect to the reflected polarization. With the above said, as the laser beam 302 is linearly polarized, rotating the λ/2 wave plate 312 to a first position allows the laser beam 302 to pass entirely through the PBSC 314 to travel along a fast path 319 and not a slow path 316 of the system 300. Rotating the λ/2 wave plate 312 by 45 degrees with respect to the first position allows the laser beam 302 to be entirely reflected by the PBSC 314 and directed to a mirror 318 so that the laser beam 302 travels along the slow path 316 and not the fast path 319. Thus, the optical switch 310 switches the laser beam 302 between the fast path 319 and the slow path 316, wherein only one path at a time is used during cutting. During the time the λ/2 wave plate 312 rotates by 45 degrees to switch between the slow path 316 and the fast path 319, the laser will be shut off. So, it will be a short delay during which the laser beam will be "off" allowing for the optical switch 310 to completely switch between the two paths.

In the fast path 319, the laser beam 302 passes through an adaptive optic device 1001 that is programmed to dynamically correct the aberrations introduced in the laser beam by refractions at various interfaces between transparent materials or tissue as the laser beam is focused at different depths and different radial positions throughout the three-dimensional working space A or B (see hashed line area A of cornea 202 of FIG. 3 and hashed line areas B in the vicinity of the anterior capsule 203 of the crystalline lens 204 of FIG. 3). After being corrected by the adaptive optic device 1001, the laser beam 302 is expanded by a beam expander 320 with a magnification equal to the ratio between the F/# of the beam directed along the slow path 316 and the F/# of the laser beam directed along the fast path 319. The expansion of the beam 302 by beam expander 320 is equivalent to expanding the entrance pupil diameter D and so the F/# is reduced. Thus, beam expander 320 acts as an F/# varying element. Note that the particular magnification for beam expander 320 is chosen in view of the fact that the beam in the slow path 316 is not expanded. The expanded laser beam 322 leaving beam expander 320 is then directed through a second PBSC 324 and passed on to an x-y-z translation device 1003. The x-y-z translation device 1003 relays the laser beam from the fast path 319 or the slow path 316 into a rotating optical system 1002 along the axis of rotation 1004 of the rotating optical system 1002. The x-y-z translation device 1003 is used to center a circular cutting pattern 1006 at desired x-y coordinates in the eye 200. The x-y-z translation device 1003 is also used to move or scan the focused laser beam 334 at the desired depth in the eye 200 along the z-axis. The laser beam 322 is relayed by the x-y-z translation device 1003 into the rotating optical system 1002, which focuses the laser beam 334 into the eye (not shown) that is being surgically repaired. The low F/# laser beam 334 focused by the scan lens system 328 is then directed by the rotating optical system 1002 to the cornea 202 or the anterior capsule 203 wherein incisions or cuts are made thereto pursuant to a predetermined pattern. The details regarding the adaptive optic device 1001, the x-y-z translation device 1003, and the rotating optical system 1002 will be explained later in the present application.

When the optical switch 310 directs light along the slow path 316, the laser beam 302 is redirected via steering mirrors 318 and 333 into the second polarization beam splitter cube (PBSC) 324. As shown in FIG. 11, the fast path 319 and the slow path 316 are recombined by the second PBSC 324 and both sent into the x-y-z translation device 1003, which further relays the laser beam into the rotating optical system 1002 along the axis of rotation 1004. The high F/# laser beam 336 focused by the rotational optical system 1002 is then directed to the crystalline lens 204 wherein incisions or cuts are made thereto pursuant to a predetermined pattern. Note that since the focused laser beam 336 formed through the slow path 316 has a higher F/#, and since a higher F/# beam is not sensitive to aberrations introduced by various refractions of the beam 336 in the eye, it is not necessary to use an adaptive optic device to correct aberrations like in the case where the focused beam 334 is formed through the fast path 319.

Note that the operation of PBSCs 314 and 324 is such that all light reflected by PBSC 314 into the slow path 316 will be reflected by PBSC 324 back onto the optical axis of the x-y-z translation device 1003 due to the polarization being parallel to the reflecting surface of both PSCs. Likewise, all light transmitted by PBSC 314 will be transmitted by PBSC 324. The advantage of using PBSCs is that the power loss is minimized through the system since they transmit or reflect all light.

Figure 12B:
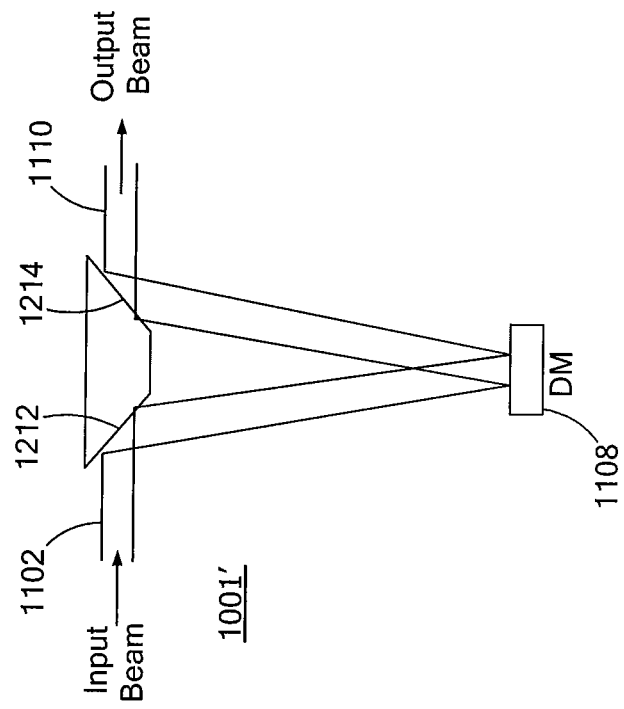
FIG. 12B schematically shows an alternate embodiment of an adaptive optical device to be used with the beam delivery optical system of FIG. 11 in accordance with the present invention.
Figure 12A:
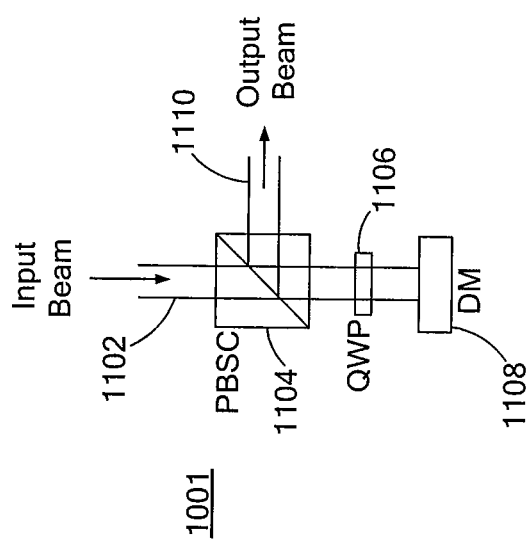
FIG. 12A schematically shows a first embodiment of an adaptive optical device to be used with the beam delivery optical system of FIG. 11 in accordance with the present invention.

The preferred embodiment of the adaptive optic device 1001 used in the beam delivery optical system 1000 of FIG. 11 is shown in FIG. 12A. In particular, a deformable mirror (DM) 1108 can be used as an adaptive optic element. Deformable mirrors are commercially available from several manufacturers, such as Imagine Optic of Orsay, France and Boston Micromachines Corporation of Cambridge, Mass. Referring to FIG. 12A, the input laser beam 1102 from PBSC 314 enters the adaptive optic device 1001 via a PBSC 1104 such that the beam is directed through a quarter wave-plate (QWP) 1106 along a path normal to the surface of the DM 1108. The QWP 1106 has the role of converting the linear polarized light of the input beam 1102 into circular polarized light, and after reflection off of the DM 1108, the QWP 1106 converts the circular polarized light back into linear polarized light. However, after the double pass through the QWP 1106, the linear polarization of an output beam 1110 turns by 90 degrees with respect to the linear polarization of the input beam 1102, so the output beam 1110 exits from the alternate facet of the PBSC 1104. The advantage of this embodiment is that the laser beam is directed normal to the DM 1108, maximizing the dynamic range of the DM 1108.

In an alternate embodiment, adaptive optic device 1001' shown in FIG. 12B can be used in the beam delivery optical system 1000 of FIG. 11, wherein the input beam 1102 is reflected by a first reflective surface 1212 into the DM 1108, then further reflected into a second reflective surface 1214, which reflects the output beam 1110.

Note that the DM 1108 can be replaced by other types of adaptive optic elements, such as a liquid crystal spatial light modulator, available from Boulder Nonlinear Systems of Lafayette, Colo. Also, note that the position of the adaptive optic device 1001, 1001' in the beam delivery optical system 1000 of FIG. 11 can be changed without departing from the spirit of the present invention. For example; the adaptive optic device 1001, 1001' can be placed anywhere along the laser beam path between the laser 304 and the optical switch 310, before or after the beam expander 320 along the laser beam in the fast path 319, or between the PBSC 324 and the rotating optical system 1002 along the laser beam.

Figure 13:
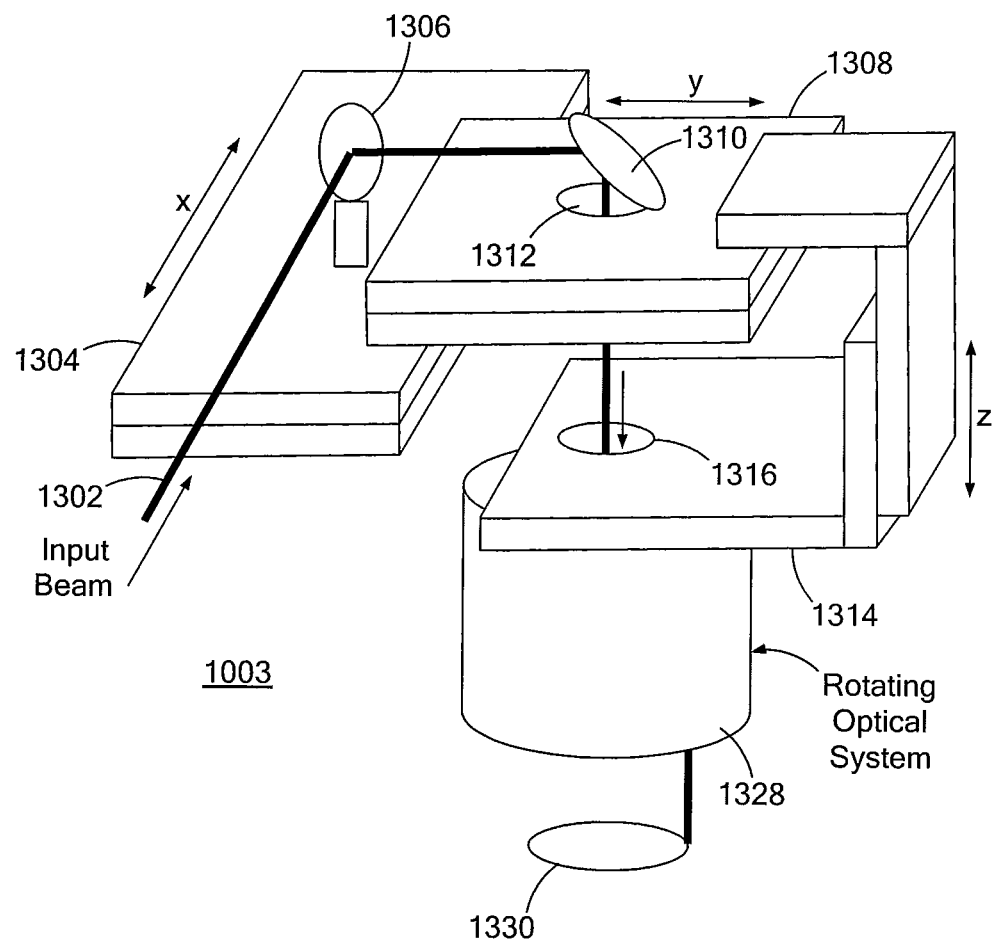
FIG. 13 schematically shows an embodiment of an x-y-z translation device to be used with the beam delivery system of FIG. 11.

The preferred embodiment of the x-y-z translation device 1003 is represented schematically in FIG. 13. The input beam 1302 from either the slow path 316 or fast path 319 enters the x-y-z translation device 1003 parallel to the x-axis of movement of a first linear translation stage 1304 and is reflected by 90 degrees by a first mirror 1306 that is mounted onto the first translation stage 1304. After the reflection off of the first mirror 1306, the beam 1302 travels parallel to the y-axis of movement of a second linear translation stage 1308 and is reflected by 90 degrees by a second mirror 1310 that is mounted onto the second linear translation stage 1308. The second linear translation stage 1308 is mounted onto the first linear translation stage 1304. As shown in FIG. 13, an aperture 1312 is formed in the center of the second linear translation stage 1308 so as to allow the beam 1302 reflected by mirror 1310 to pass therethrough. After the reflection off of the second mirror 1310, the beam 1302 travels parallel to the z-axis of movement of a third linear translation stage 1314, through an opening 1316 of the third linear translation stage 1314, and along the axis of rotation of the rotating optical system 1002. The x-, y- and z-axes of movement are perpendicular to one another.

Other embodiments for the x-y-z translation device are possible. For example; the x-y-z staggered linear translation stages of FIG. 13 could be replaced by a motorized hexapod structure and the laser beam could be relayed into the rotating optical system 1002 by an articulated opto-mechanical arm that would allow translation of the beam in the x-y-z directions. Another method to translate the laser beam is to eliminate the x-y-z translation device 1003 and place the entire laser system (including laser source and rotating optical system) on a platform capable of moving in the x-y-z directions.

Figure 14:
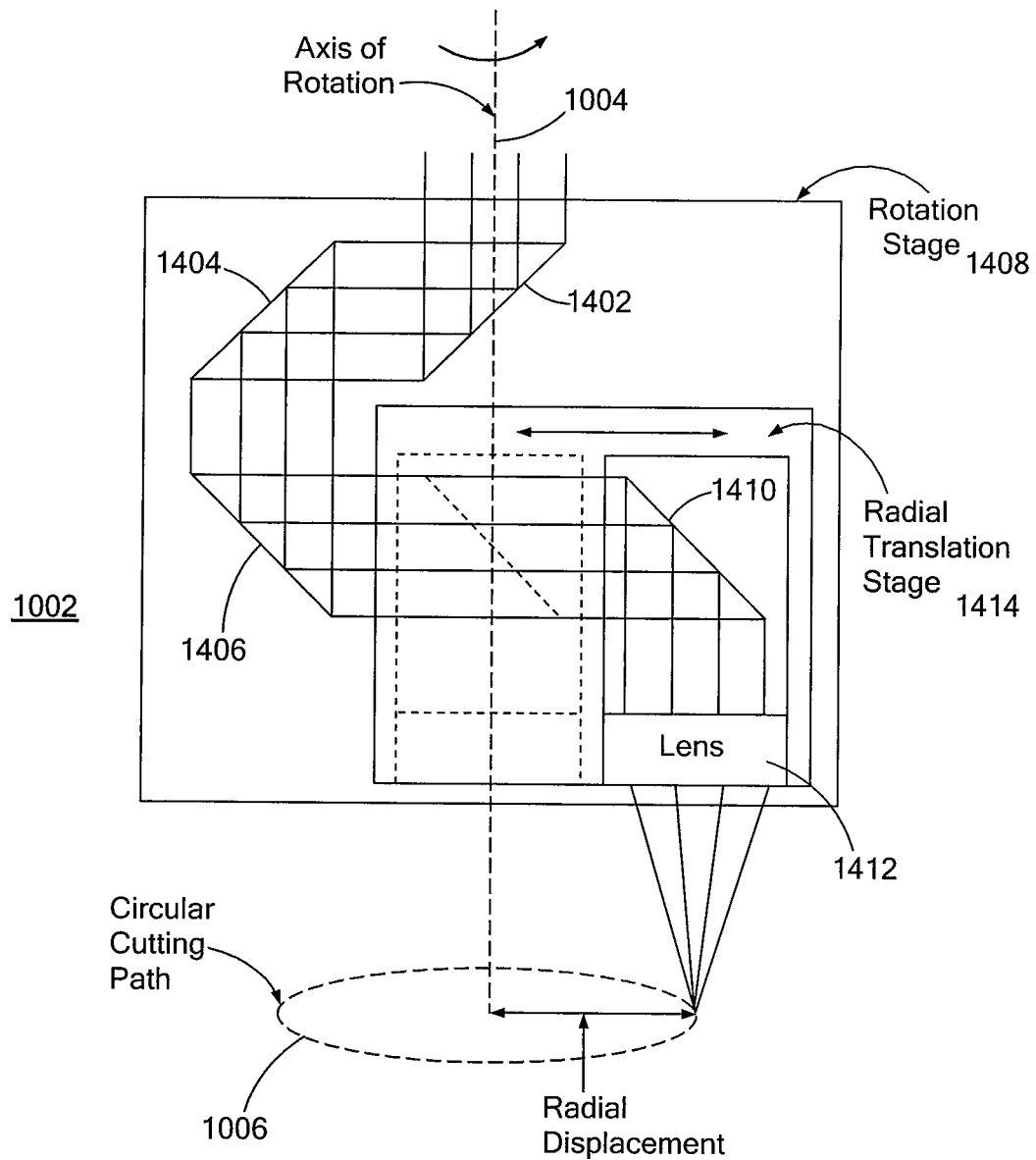
FIG. 14 schematically shows an embodiment of a rotating optical system to be used with the beam delivery system of FIG. 11.

The preferred embodiment of the rotating optical system 1002 is represented schematically in FIG. 14. The first three mirrors 1402, 1404, 1406 in the rotating optical system are fixed with respect to the rotation stage 1408 (an alternate embodiment for these three fixed mirrors can be a multi-facet prism with three reflective surfaces). A fourth mirror 1410 is mounted together with a focusing lens 1412 onto a radial displacement linear stage 1414 (7-8 mm total motion range), which is mounted to the rotation stage 1408. The laser beam generated from the fast path 319 or the slow path 316 is relayed from the x-y-z translation device 1003 into the rotating optical system 1002 along the axis of rotation. The laser beam is reflected by the first three mirrors 1402, 1404, 1406 as shown in FIG. 14 and relayed into the fourth mirror 1410, which directs the laser beam through the focusing lens 1412. When the radial displacement linear stage 1414 is at its 0 position, the focus of the laser beam remains stationary while the rotation stage is in motion. As the radial displacement linear stage 1414 moves away from the axis of rotation by an amount R, the focus of the laser beam describes a circle 1330 of radius R while the rotation stage 1002 is in motion.

Figure 15:
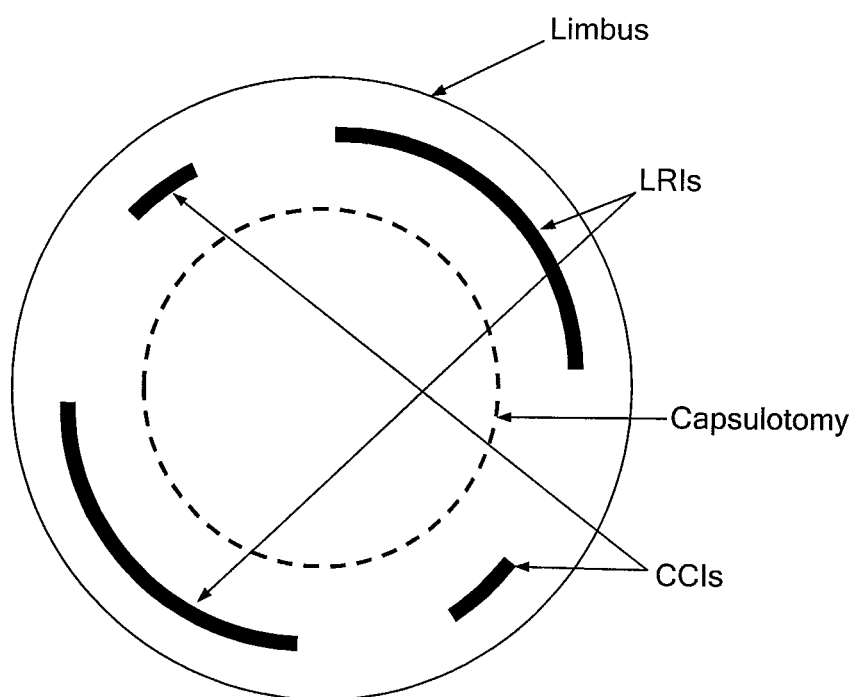
FIG. 15 shows a top view of typical circular incisions/cuts patterns in the case where the beam is formed through the fast path.

Cuts or incisions formed in the eye that are rotationally symmetric about the axis of rotation can be performed at arbitrary radial positions and z depths (within the range of the linear translation stages) using the radial displacement linear stage 1414 in the rotating optical system 1002 in conjunction with the z linear stage in the x-y-z translation device 1003. Therefore, the ophthalmic laser system described in the present invention is ideal for performing cuts or incisions in the cornea and anterior capsule of the crystalline lens (such as CCIs, LRIs, and capsulotomy), which are typically rotationally symmetric patterns about the apex of the cornea or about the apex of the anterior capsule of the crystalline lens. FIG. 15 shows a top view of typical arcuate incisions/cuts that are made along one or more circular patterns in the case where the beam is formed through the fast path 319.

Figure 16B:
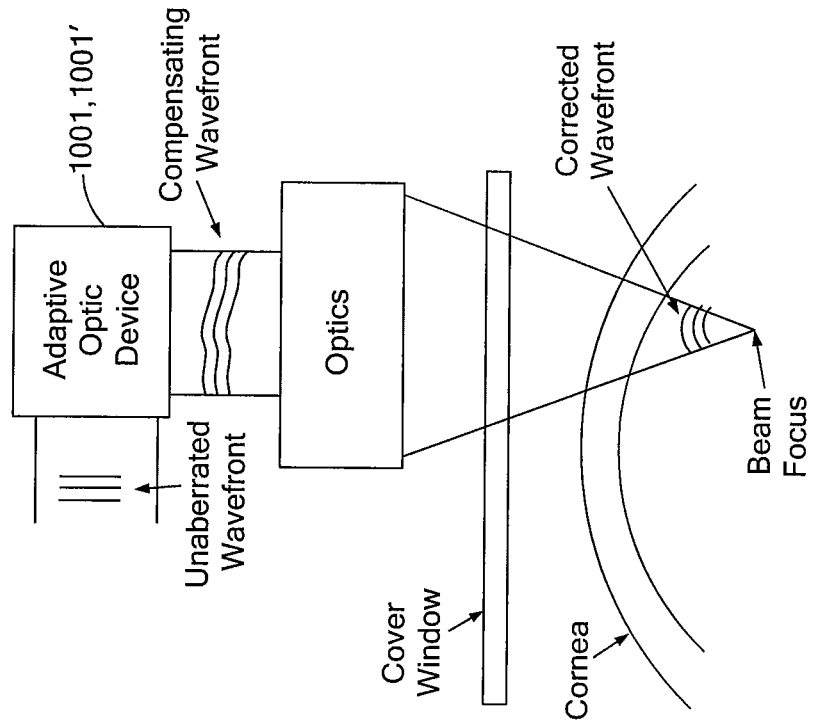
FIG. 16B schematically represents the case where the unaberrated wavefront of FIG. 16A is corrected by either one of the adaptive optical devices of FIGS. 12A-B so that aberrations introduced in the laser beam by refractions at various transparent interfaces are corrected by the adaptive optic device.
Figure 16A:
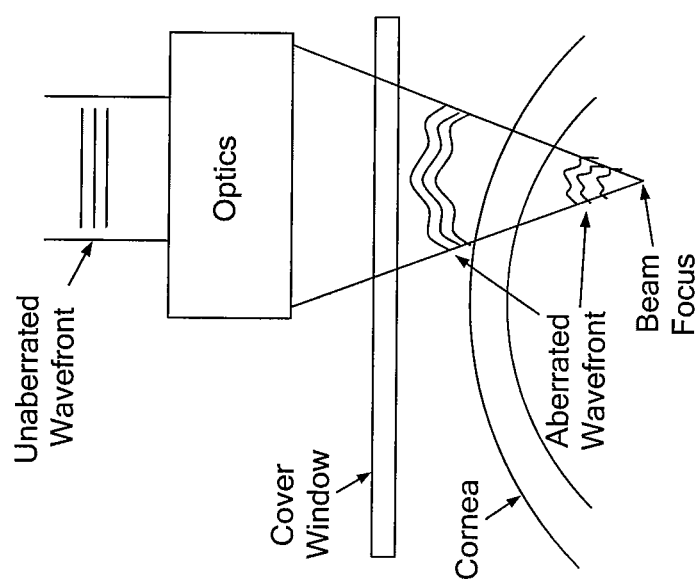
FIG. 16A schematically represents an example where an unaberrated wavefront is directed to optics which results in aberrated wavefronts after passing through a cover window, a cornea and other portions of an eye before arriving at a focal point.

However, all the above mentioned cuts or incisions in the eye are done with a fast laser beam, and therefore the aberrations in the laser beam would have to be corrected using the adaptive optic device 1001, 1001' in conjunction with the real-time position of the beam focus (waist) into the eye. After the three-dimensional biometrics are measured for the eye to be treated (all positions, thicknesses, and radii of curvature of the cornea, anterior chamber, and crystalline lens), the desired patterns of all cuts and incisions are programmed into the system. Then, the optical aberrations introduced in the laser beam due to refractions through the transparent tissue are calculated theoretically and mapped throughout the three-dimensional space based on the biometrics and the programmed cuts and incisions patterns. Aberrations in the laser beam will vary with the position of the focus in z (controlled by the z stage 1314 in the x-y-z translation device 1003), radial displacement (controlled by the radial displacement linear stage 1414 in the rotating optical system 1002), and azimuth angle (controlled by the position of the rotating stage 608). The adaptive optic device 1001, 1001' is then programmed to correct these aberrations in real time as a function of the three-dimensional position of the laser beam focus with respect to the measured biometrics. FIG. 16A schematically represents the case where an unaberrated wavefront is directed to optics which results in aberrated wavefronts after passing through a cover window, a cornea and other portions of an eye before arriving at a focal point. FIG. 16B schematically represents an example where, in the case where the beam is formed through the fast path, the aberrations introduced in the laser beam by refractions at various transparent interfaces are corrected by the adaptive optic device. Note that the adaptive optic device 1001, 1001' will have to dynamically change the compensating wavefront in real-time to follow the change in aberrations with the relative position of the laser beam focus into the treated eye.

In the case of the crystalline lens fragmentation cuts, which are done with the slow laser beam (large F/#), transversal arc shaped cuts are typically used along with circular cuts to form pie shaped pieces (see triangular-like pieces near center of pattern) and rectangular-like pieces (see pieces positioned away from center of pattern) as shown schematically in FIG. 17A. A possible process for forming the circular cuts of FIG. 17A would be to turn off the laser and move the axis of rotation of the optical system 1002 via the x-y-z translation device 1003 so as to coincide with the axis of the eye. Next, the radial position of the laser beam (either 334, 336) emitted from the optical system 1002 is controlled by translating the radial translation stage 1414. Next, the z-position of the focus of the laser beam is controlled by the linear translation stage 1314 of the x-y-z-translation device 1003. Once the radial and z positions are set, the laser is turned on and full rotation of the rotating stage 1408 results in a circular cut being formed at a particular depth of the eye. Other circular cuts can be formed by varying the depth of the focused laser beam in the eye and varying the radius of rotation by moving the linear translation stage 1314 and rotating stage 1408.

As shown in FIG. 17A, pie-shaped pieces and rectangular-like pieces can be formed by the previously described circular cuts and transversal arc-shaped cuts that are transverse to the circular cuts. With the above said, the laser is turned off and a desired radius of curvature of the transversal arc-shaped cut is obtained by varying the radial translation stage 1414 until the desired radius of curvature is achieved. Next, the path of the transversal arc-shaped cut is selected by translating the axis of rotation of the optical system 1002 to a position so that the cut will intersect the center of the eye and two points on the maximum fragmentation diameter (see FIG. 17B). Next, the rotating stage 1408 is rotated so that when the laser is turned on, the laser beam is focused at one of the two points mentioned previously. The rotating stage 1408 continues to rotate while the laser beam follows an arcuate path until it reaches the second point at which the laser is turned off. Other transversal arc-shaped cuts can be formed by varying the depth of the focused laser beam in the eye by moving the linear translation stage 1314. Other transversal arc-shaped cuts can be formed by turning the laser off and translating the axis of rotation of the optical system 1002 other positions by moving the linear stages 1304 and 1308.

Note that other embodiments for a dual beam delivery optical system are possible. An example of such an optical system is the beam delivery optical system 1500 shown in FIG. 18. The structure of beam delivery optical system 1500 is similar to beam delivery optical system 1000 of FIG. 11. In particular, a laser beam 302 is generated by a laser source 304 and directed via mirrors 306, 308 to an optical switch 310. In contrast to the λ/2 wave plate 312 and polarization beam splitter cube (PBSC) 314 of FIG. 11, the system 1500 uses a turning mirror 1502 that can rotate to a first position so that the laser beam 302 is directed to mirror 318 and the slow path in a manner as described with respect to the embodiment of FIG. 11. Rotating turning mirror 1502 causes the laser beam 302 to reflect off of mirror 1504 and directed to the fast path to be processed by the adaptive optic device 1001, 1001' and the beam expander 320 in a manner as described with respect to the embodiment of FIG. 11.

Figure 18:
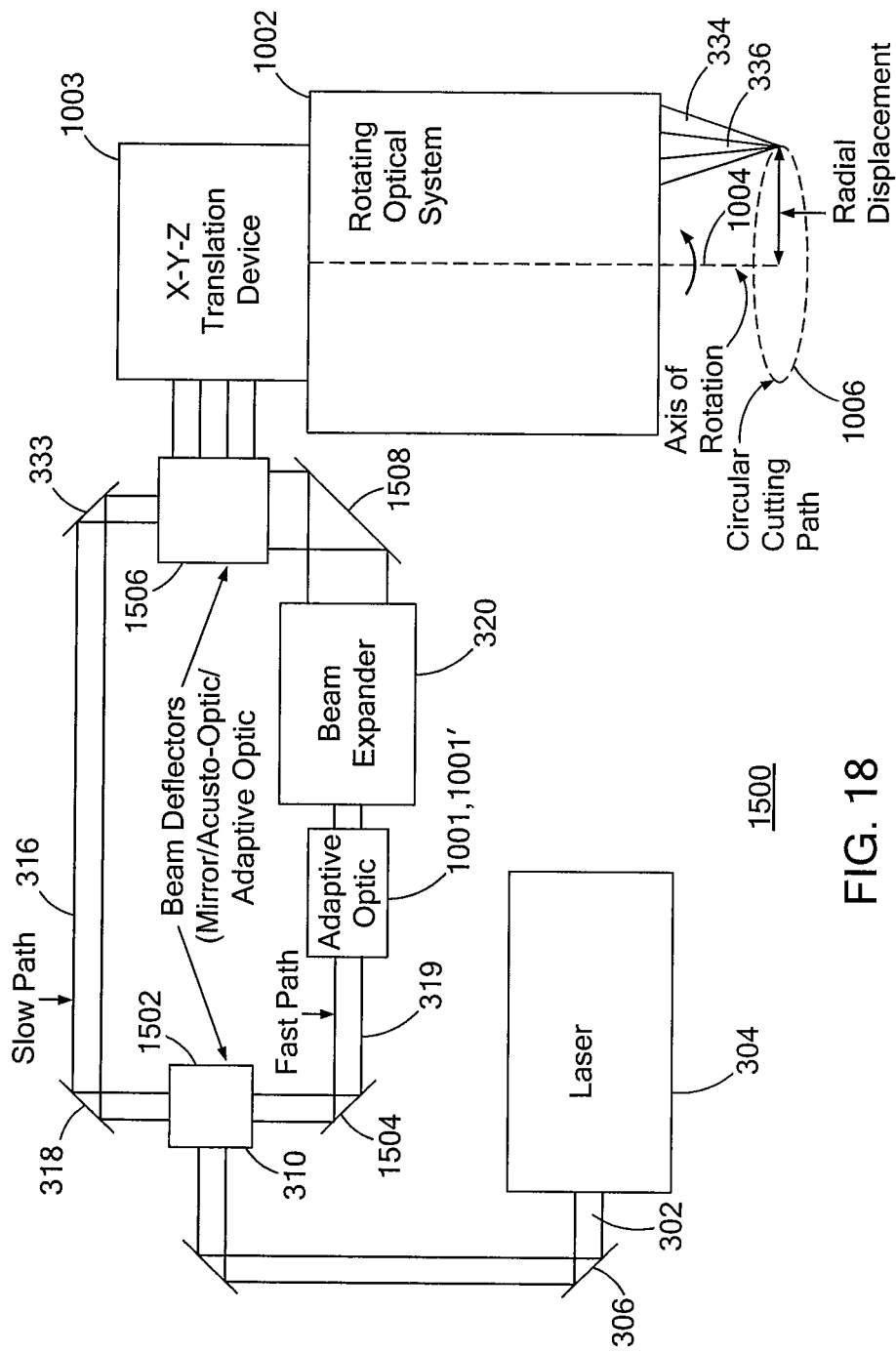
FIG. 18 schematically shows a sixth embodiment of a beam delivery optical system in accordance with the present invention.

As shown in FIG. 18, the fast path laser beam is deflected by a mirror 1508 to a second turning mirror 1506 which is positioned at a first position to reflect the fast path laser beam to the x-y-z translation device 1003. Similarly, the slow path laser beam is deflected by a mirror 333 to the turning mirror 1506 which is positioned at a second position to reflect the slow path laser beam to the x-y-z translation device 1003. The slow path and fast path laser beams are processed, relayed and focused by the adaptive optic device 1001, 1001', x-y-z translation device 1003 and rotating optical system 1002 in a manner similar to that described with respect to the embodiment of FIG. 11.

Note that in operation, the rotation of mirrors 1502 and 1506 are synchronized so that the laser beam 302 passes through either only the fast path 319 or the slow path 316. In addition, the laser beam 302 is stopped or the laser 304 is shut off during rotation of the mirrors 1502 and 1506.

Other possibilities for the optical switch 310 of FIG. 15 are possible. For example, the mirrors 1502 and 1506 can be replaced by acusto-opto deflectors, adaptive optics deflectors or regular beam splitters (50/50 splitters, for example). In the case of using regular beam splitters, portions of the laser beam 302 will be present in both the fast path 319 and the slow path 316. Shutters are present in each of the fast and slow paths so that one is closed at any moment of time, the laser beam will travel in the path that is not closed.

Figure 19:
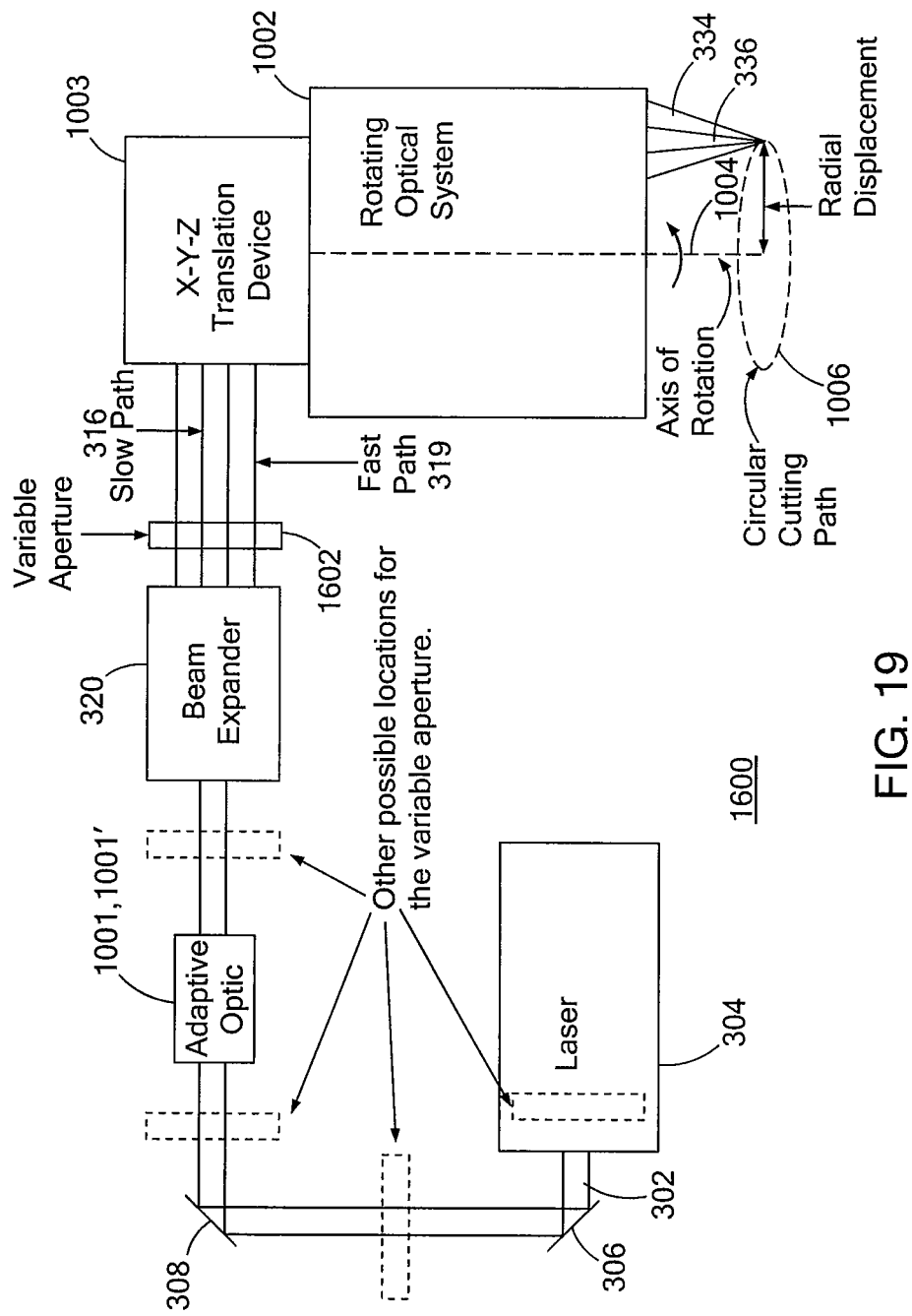
FIG. 19 schematically shows a seventh embodiment of a beam delivery optical system in accordance with the present invention.
Figure 20:
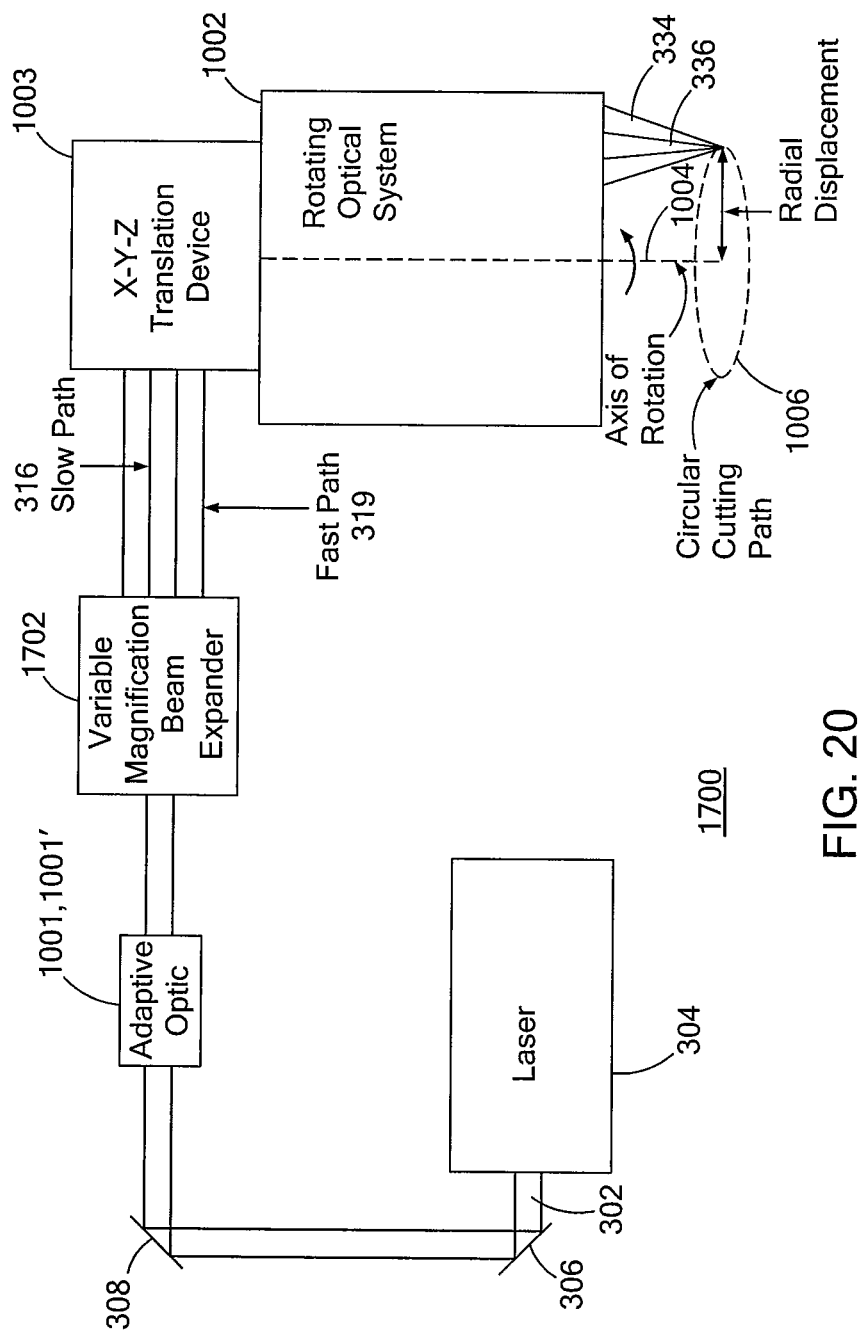
FIG. 20 schematically shows an eighth embodiment of a beam delivery optical system in accordance with the present invention.

The previously described systems 1000 and 1500 of FIGS. 11 and 18 operated on the principle of separating the fast and slow laser beams in separate paths. As shown in FIGS. 19 and 20, it is possible to generate fast and slow laser beams on a common path. Regarding the embodiment shown in FIG. 19, a beam delivery optical system 1600 includes a laser beam 302 that is generated by a laser source 304 and directed via mirrors 306, 308 to an adaptive optic device 1001, 1001' and a beam expander 320. As shown in FIG. 19, the laser beam 302 is transformed by a variable aperture 1602 that can be positioned at various locations along the single path. In operation, the variable aperture 1602 is controlled to have a first aperture size that will generate a laser beam with a F/# that has a value that is similar to the laser beam present in the slow paths of the systems 1000 and 1500 of FIGS. 11 and 18. The variable aperture 1602 can also be controlled to have a second aperture size that will generate a laser beam with a F/# that has a value that is similar to the laser beam present in the fast paths of the systems 1000 and 1500 of FIGS. 11 and 18. After the particular laser beam (fast or slow) is formed, it passes through the x-y-z translation device 1003 and the rotating optical system 1002 in a manner similar as described previously with respect to systems 1000 and 1500 of FIGS. 11 and 18.

Note that in the alternate embodiment of FIG. 20, a beam delivery optical system 1700 is nearly identical to that of system 1600 of FIG. 19 wherein variable aperture 1602 is replaced by a variable magnification beam expander 1702, such as the Motorized Zoom Beam Expander Models VIS-NIR 56C-30-1-4x-λ and 2-8X-λ, manufactured and sold by Special Optics of Wharton, N.J. Instead of varying an aperture size to generate different F/# laser beams as in FIG. 19, the beam expander 1702 changes the magnification of the laser beam so as to have different F/# values. Thus, system 1700 operates in a manner similar to that of system 1600. Note that beam expander 1702 can also be positioned within laser 304, between laser 304 and mirror 306, between mirrors 306 and 308, and between mirror 308 and adaptive optic 1001, 1001'.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims. For example, other optical elements can be used for switching between the fast and slow paths of FIGS. 4, 8-11 and 18-20. In addition, additional optical configurations and/or elements can be used for items 332, 328 and/or 1002 of FIGS. 4, 8-11, 14 and 18-20 without departing from the spirit of the invention.

We claim:

1. An ophthalmic laser system comprising:
    a laser source that generates a laser beam;
    an optical switch that receives said laser beam and selectively sends said laser beam to either a fast path or a slow path, wherein in said fast path said laser beam has a first F/# and in said slow path said laser beam has a second F/# that is higher in value than said first F/#;
    an adaptive optic device that is in said fast path and receives said laser beam from said optical switch;
    an x-y-z translation device that receives either a first laser beam from said slow path or a second laser beam from said fast path; and
    a rotating optical system that receives a laser beam from said x-y-z translation device and performs a partial or full circular scan of said received laser beam about an axis of rotation of said rotating optical system, wherein said rotating optical system is able to translate so as to vary a radius of said partial or full circular scan and said partial or full circular scan is positioned in an eye of a patient; and
    wherein said adaptive optic corrects said laser beam received from said fast path so that aberrations at said partial or full circular scan are significantly reduced.

2. The ophthalmic laser system of claim 1, wherein said optical switch comprises a λ/2 wave plate and a polarization beam splitter cube in series with one another.

3. The ophthalmic laser system of claim 1, wherein said optical switch comprises a turning mirror that can rotate to a first position so that said laser beam is directed to said slow path and can rotate to a second position so that said laser beam is directed to said fast path.

4. The ophthalmic laser system of claim 1, wherein said optical switch comprises an acusto-opto deflector.

5. The ophthalmic laser system of claim 1, wherein said optical switch comprises an adaptive optics deflector.

6. The ophthalmic laser system of claim 1, wherein said optical switch comprises a regular beam splitter.

7. The ophthalmic laser system of claim 1, further comprising a beam expander in the fast path that receives said laser beam from said optical switch.

8. The ophthalmic laser system of claim 7, wherein a magnification of a laser beam generated by said beam expander is equal to the ratio: first F/#/second F/#.

9. The ophthalmic laser system of claim 1, wherein said adaptive optic comprises a beam splitting device that receives from said optical switch said laser beam in said fast path and directs said laser beam in said fast path to a deformable mirror and said deformable mirror redirects said laser beam in said fast path to said beam splitting device which in turn directs said laser beam toward said x-y-z translation device.

10. The ophthalmic laser system of claim 9, wherein said beam splitting device comprises a polarization beam splitter cube.

11. The ophthalmic laser system of claim 10, further comprising a quarter wave plate that receives said laser beam in said fast path from said beam splitting device and directs said laser beam in said fast path to said deformable mirror.

12. The ophthalmic laser system of claim 9, wherein said rotating optical system comprises:
    a rotation stage that rotates about said axis of rotation and receives either said first laser beam or said second laser beam from said x-y-z translation device; and
    a radial translation stage is positioned within said rotation stage so as to rotate with said rotation stage, wherein said radial translation stage translates relative to said rotation stage and comprises a lens that receives and focuses either said first laser beam or said second laser beam from said rotation stage.

13. The ophthalmic laser system of claim 1, wherein said rotating optical system comprises:
    a rotation stage that rotates about said axis of rotation and receives either said first laser beam or said second laser beam from said x-y-z translation device; and
    a radial translation stage is positioned within said rotation stage so as to rotate with said rotation stage, wherein said radial translation stage translates relative to said rotation stage and comprises a lens that receives and focuses either said first laser beam or said second laser beam from said rotation stage.

14. An ophthalmic laser system comprising:
    a laser source that generates a laser beam;
    an optical switch that receives said laser beam and selectively transforms said laser beam to either a fast path laser beam or a slow path laser beam, wherein said fast path laser beam has a first F/# and said slow path laser beam has a second F/# that is higher in value than said first F/#;
    an adaptive optic device that receives either said fast path laser beam or said slow path laser beam from said optical switch;
    an x-y-z translation device that receives either said fast path laser beam or said slow path laser beam from said adaptive optic; and
    a rotating optical system that receives a laser beam from said x-y-z translation device and performs a partial or full circular scan of said received laser beam about an axis of rotation of said rotating optical system, wherein said rotating optical system is able to translate so as to vary a radius of said partial or full circular scan and said partial or full circular scan is positioned in an eye of a patient; and
    wherein said adaptive optic corrects said fast laser beam so that aberrations along said partial or full circular scan are significantly reduced.

15. The ophthalmic laser system of claim 14, wherein said optical switch comprises a beam expander.

16. The ophthalmic laser system of claim 14, wherein said optical switch comprises a variable magnification beam expander.

17. A method of surgically repairing an eye comprising:
    generating a laser beam;
    selectively manipulating said laser beam so that said laser beam is present in either a fast path or a slow path, wherein in said fast path said laser beam has a first F/# and in said slow path said laser beam has a second F/# that is higher in value than said first F/#;
    having an adaptive optic device that is in said fast path to receive said selectively manipulated laser beam in said fast path;
    having an x-y-z translation device that receives either said fast path laser beam or said slow path laser beam from said adaptive optic;
    receiving a laser beam from said x-y-z translation device and performing a partial or full circular scan of said received laser beam and varying a radius of said circular scan, wherein said partial or full circular scan is positioned in an eye of a patient, and wherein said adaptive optic corrects said laser beam received from said fast path so that aberrations along said partial or full circular scan are significantly reduced.

* * * * *